(12) United States Patent
Melvin et al.

(10) Patent No.: US 8,753,392 B2
(45) Date of Patent: Jun. 17, 2014

(54) ELEMENTS FOR VERSATILITY OF A PROSTHETIC ANCHOR

(75) Inventors: David B. Melvin, Loveland, OH (US); Sue P. Melvin, legal representative, Loveland, OH (US); Alan Joel Melvin, Cincinnati, OH (US); Jeffrey Franklin, Hamilton, OH (US)

(73) Assignee: University of Cincinnati, Cincinnati, OH (US)

( * ) Notice: Subject to any disclaimer, the term of this patent is extended or adjusted under 35 U.S.C. 154(b) by 117 days.

(21) Appl. No.: 13/290,700

(22) Filed: Nov. 7, 2011

(65) Prior Publication Data

US 2012/0109166 A1    May 3, 2012

Related U.S. Application Data

(63) Continuation-in-part of application No. 11/813,469, filed as application No. PCT/US2006/000555 on Jan. 9, 2006, now Pat. No. 8,052,753.

(60) Provisional application No. 60/642,016, filed on Jan. 7, 2005.

(51) Int. Cl.
*A61F 2/08*    (2006.01)

(52) U.S. Cl.
USPC ............ 623/13.14; 623/13.11; 623/13.2

(58) Field of Classification Search
USPC ........... 623/13.11, 13.14, 13.17, 13.18, 13.2, 623/14.12, 15.11, 23.51; 604/399; 606/232, 606/187, 286
See application file for complete search history.

(56) References Cited

U.S. PATENT DOCUMENTS 7,601,165 B2 *  10/2009  Stone .......................... 606/232

* cited by examiner

*Primary Examiner* — David Isabella
*Assistant Examiner* — Yashita Sharma
(74) *Attorney, Agent, or Firm* — Wood, Herron & Evans, LLP

(57) ABSTRACT

A prosthetic anchor to be attached to a natural or prosthetic structure of a human or animal. The anchor includes a central layer with first and second surface. A plurality of fiber bundles, each with a medial portion, are concentrically embedded within the central layer to substantially define a horseshoe-shaped pattern. A substrate element is configured to be secured to the natural or prosthetic structure and to receive the second surface of the central layer. A securing element operably coupled to the second surface of the central layer is configured to secure the central layer to the substrate element in at least two positions.

8 Claims, 26 Drawing Sheets

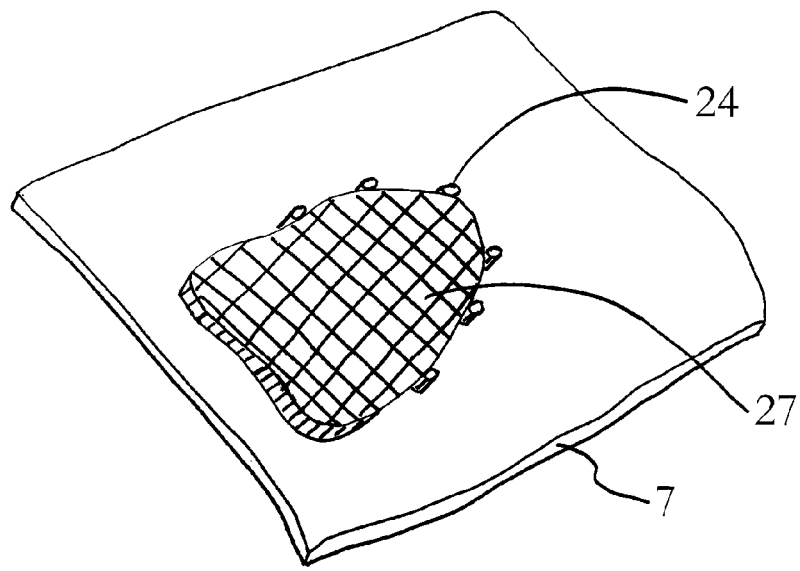
Figure 13a
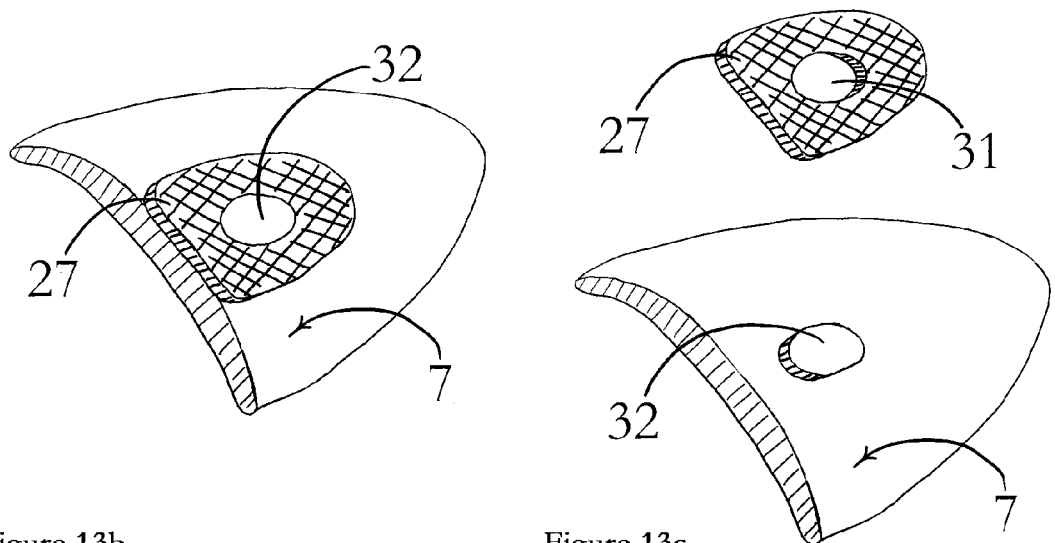
Figure 13b
Figure 13c

ELEMENTS FOR VERSATILITY OF A PROSTHETIC ANCHOR

RELATED APPLICATIONS

The present application is a continuation-in-part of U.S. patent application Ser. No. 11/813,469, filed Jul. 8, 2008, entitled "PROSTHETIC ANCHOR AND METHOD OF MAKING SAME", to be issued U.S. Pat. No. 8,052,753, which is a U.S. National Stage Application of International Application No. PCT/US2006/000555 filed on Jan. 9, 2006, entitled "PROSTHETIC ANCHOR AND METHOD OF MAKING SAME", which claims the filing benefit of U.S. Provisional Application Ser. No. 60/642,016 filed on Jan. 7, 2005, entitled "PROSTHETIC ANCHOR AND METHOD OF MAKING SAME", the application, patent and disclosures of which are all incorporated herein by reference in their entireties.

FIELD OF THE INVENTION

The present invention relates generally to fixation devices and methods of transmitting force from skeletal muscles, to energy converters powering cardiac or other devices, to a prosthetic, or to a natural bone, and relates more particularly to prosthetic devices having improved stress distribution in a fixed tension member.

BACKGROUND OF THE INVENTION

Fixation of prosthetic flexible tension members, such as tendons or ligaments, to relatively rigid structures remains a difficult problem. A notable example is the use of artificial ligaments, such as the Leeds-Keio anterior cruciate ligament replacement in the knee. In that example, surgeons using the conventional surgical procedure of bone fixation—drilling a hole in the tibia, inserting the ligament, and securing with a suture or pin—have reported instances of fragmentation of the polyester fibers of the prosthesis within a few months to a few years. A compression plate has also been conventionally used, whereby tension members are cut and the ends are secured between two plates that may be textured and held together by compression screws. While this allows greater control of local stress concentration than the simple bone-hole, in theory the compression plate delivers extremely high shear stresses to the tension member locally, which may cause fatigue failure and breakage over a number of stress cycles.

A knob-loop fixation device has been described previously (pending patent application Ser. No. 12/678,008) to address the stress-concentration issue, but requires a substantial thickness that may be disadvantageous. Such thickness may be problematic in some cardiac, plastic, reconstructive, or orthopaedic surgical applications, particularly in regions where the skin is quite close to the bone (e.g., the frontal bone in the case of a cosmetic surgical "brow lift" or the olecrenon in an orthopaedic surgical elbow prosthesis).

Further, complications occur in that the surface to which the fixation device is attached may vary in its contour. Therefore a thinner fixation device having sufficient flexibility to allow a finite number of size/shape models conformable to anatomical variations would be of benefit. Further, a structure having a soft flexible interface to fibers (reducing stress concentration) with a harder external surface (to interface with other tissues) would also be advantageous.

Natural tendon ends, which are living tissue, have been conventionally connected to a "towel bar" fixture on artificial bones, over which the tendons are looped and sewn. Because of the shape of tendons—generally flattened in the plane of attachment, the axis of curvature is generally perpendicular to the surface to which the tendons are to be attached. To avoid intolerable protrusion into surrounding tissue structures, the radius of curvature is generally small. Since the compressive stress on the surface of a tension member about any rod or pulley, is directly proportional to the tension applied and inversely proportional to both the radius of curvature and the projection of contact surface perpendicular to the transmitted tension, compressive forces that are intolerable by the tension member may be generated. However, an artificial force transmitting tension member, such as an artificial tendon, may be formed in any cross-sectional configuration. This allows the looped portion to be relatively thin, flat, and oriented in the plane of the surface to which the tension member is to be attached.

Further, some clinical situations are anticipated where the following improvements may increase the versatility or practicality of such devices: (1) alternative or supplemental methods of adjusting the length of and/or tension in a repair or surgical construct by a fixation device, (2) a reduction in the thickness of the hardware in a medial portion of the fixation device, and (3) an elongated tension element configured to transmit a force from a muscle to a distant location that preserves a continuity of the prosthetic fibers from within the muscle to the distant location and thus avoids mechanical weaknesses of otherwise required connections.

SUMMARY OF THE INVENTION

The present invention overcomes the foregoing problems and other shortcomings, drawbacks, and challenges of prosthetic anchors. While the present invention will be described in connection with certain embodiments, it will be understood that the present invention is not limited to these embodiments. To the contrary, this invention includes all alternatives, modifications, and equivalents as may be included within the spirit and scope of the present invention.

In accordance with one embodiment of the present invention, a prosthetic anchor to be attached to a natural or prosthetic structure of a human or animal includes a central layer with a plurality of fiber bundles. The anchor includes a central layer with first and second surfaces, and each of the plurality of fiber bundles has a medial portion. The medial portions are concentrically embedded within the central layer to substantially define a horseshoe-shaped pattern. A substrate element is configured to be secured to the natural or prosthetic structure and to receive the second surface of the central layer. A securing element operably coupled to the second surface of the central layer is configured to secure the central layer to the substrate element in at least two positions.

According to another embodiment of the present invention, a prosthetic anchor to be attached to a natural or prosthetic structure of a human or animal includes a central layer with a plurality of fiber bundles. The anchor includes a central layer with first and second surfaces, and each of the plurality of fiber bundles has a medial portion. The medial portions are concentrically embedded within the central layer to substantially define a horseshoe-shaped pattern. A first partial envelope is operably coupled to a first side of the wafer-like structure. A second partial envelope is operably coupled to a second side of the wafer-like structure. The first and second partial envelopes are configured to provide rigidity to the central layer and each is operable to interface with at least one of the natural hard surface, the prosthetic hard surface, and a tissue.

The features and objectives of the present invention will become more readily apparent from the following Detailed Description taken in conjunction with the accompanying drawings.

BRIEF DESCRIPTION OF THE DRAWINGS

The accompanying drawings, which are incorporated in and constitute a part of this specification, illustrate embodiments of the present invention and, together with a general description of the invention given above, and the detailed description given below, serve to explain the present invention.

DETAILED DESCRIPTION OF THE INVENTION

Figure 1:
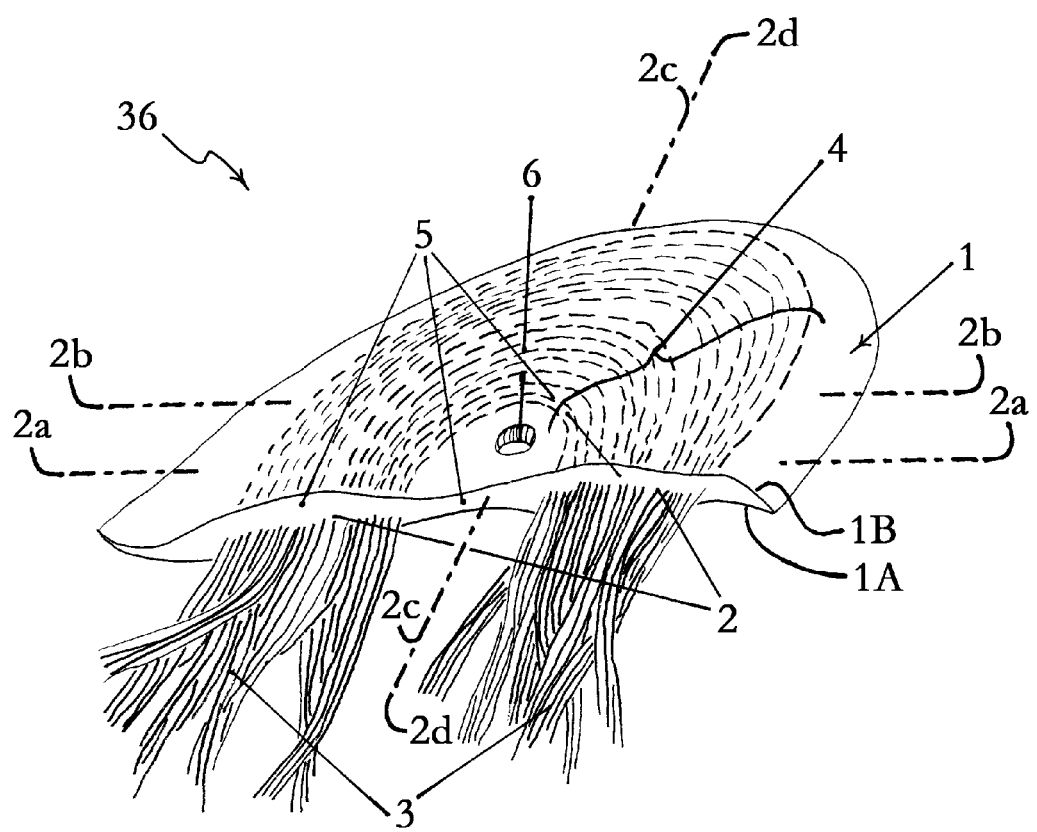
FIG. 1 is a perspective view of a central layer of a prosthetic anchor in accordance with one embodiment of the present invention.
Figure 2A:
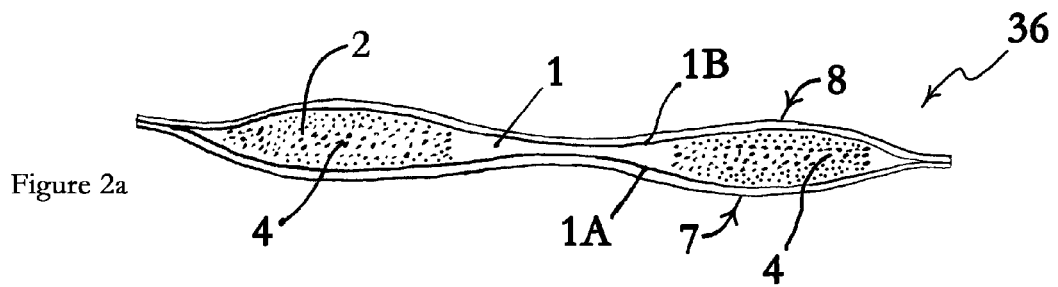
FIG. 2a is a cross-sectional view of the central layer with surface membranes taken along line 2a-2a of FIG. 1 to provide a prosthetic anchor in accordance with one embodiment of the present invention.
Figure 2B:
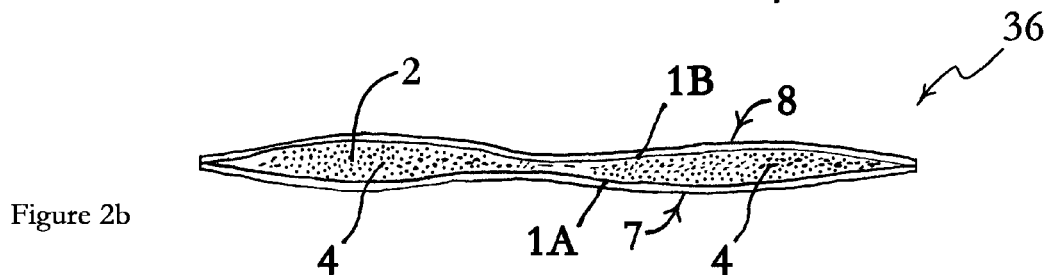
FIG. 2b is a cross-sectional view of the central layer with membranes taken along line 2b-2b of FIG. 1 to provide a prosthetic anchor in accordance with one embodiment of the present invention.
Figure 2C:
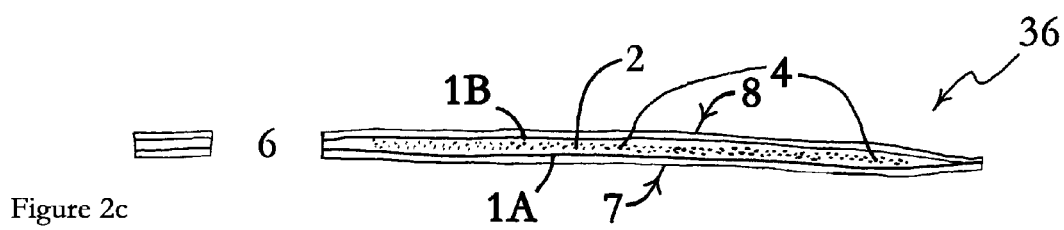
FIG. 2c is a cross-sectional view of the central layer with membranes taken along line 2c-2c of FIG. 1 to provide a prosthetic anchor in accordance with one embodiment of the present invention.
Figure 2D:
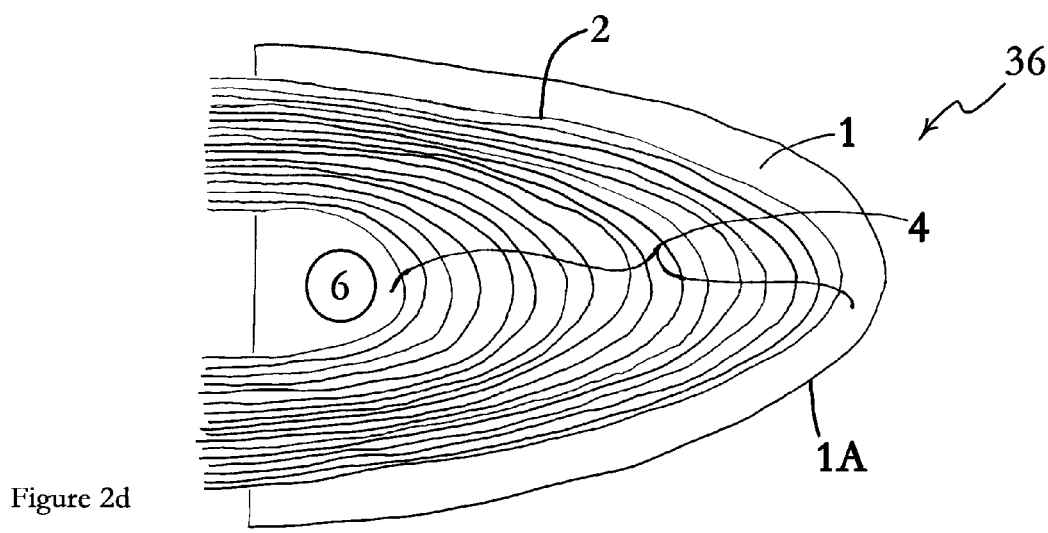
FIG. 2d is another sectional view of the central layer taken along line 2d-2d, of FIG. 1 illustrating a portion that is between the two surface membranes of FIGS. 2a-2c to provide a prosthetic anchor in accordance with one embodiment of the present invention.

In contrast to the conventional devices and methods for prosthetic fixation, the anchor in accordance with the various embodiments of the present invention, as provided herein, includes a radius of curvature that provides only a minimal protrusion into surrounding tissue structures and that does not require fibers to be organized into a circular cross-section. While the number of fibers is related to the cross-sectional area of the bundle, the actual cross-section may vary and be quite thin or otherwise configured for adjoining to an anatomic structure (e.g., a bone).

Turning now to the figures, the reference numbers provided therein include:

1. a central layer; 1a. an opposing first surface of the central layer (1); 1b. an opposing second surface of the central layer (1);
2. embedded fibers;
3. portions of the fiber bundles (2) entering and exiting the central layer (1);
4. concentric pathways of the fibers (2) in central layer (1);
5. thickened edge of the central layer (1) at which the fiber bundles enter the central layer (1);
6. optional central opening in the central layer (1);

7. a deep (semi-rigid) membrane;
8. a superficial (semi-rigid) membrane;
9. a face of the deep membrane (7) configured to adhere to the central layer (1);
10. a face of the superficial membrane (8) configured to adhere to the central layer (1);
11. a face of the deep membrane (7) configured to adhere to a bone or to a prosthesis;
12. a face of the superficial membrane (8) configured to resist adherence with a contiguous living tissue;
13. a surface, or a surface replica;
14. a mold made to mate with the surface or surface replica (13) and constructed from a soft elastomeric material, such as a polyurethane or silicone rubber. The mold (14) may also be referred to herein as a "fabrication part A";
15. a replica of the applicable surface of the surface (13). The replica (15) may also be referred to herein as a "fabrication part B";
16. a wafer configured to be manipulated to a geometry of the device. The wafer (16) may also be referred to herein as a "fabrication part C";
17. a hard outer cast formed to mate with the replica (15) and the wafer (16). The outer cast (17) may also be referred to herein as a "fabrication part D";
18. an inner section of the outer cast (17). The inner section (18) may also be referred to herein as a "fabrication part E";
19. an outer section of the outer cast (17). The outer section (19) may also be referred to herein as "fabrication part F";
20. a removable pin;
21. a smooth surface of a composite membrane;
22. a metal mesh insert in the deep surface of the deep membrane (7);
23. a textured metal plate insert incorporated into the deep surface (11) of the deep membrane (7) 7;
24. short needle-like projections;
25. a peg-like central plateau;
26. a roughened and textured superficial surface (9) of the deep composite membrane (7);
27. a generally parabolic disc of fabric or other porous biocompatible material;
28. tows or bundles of coupler fibers;
29. individual coupler fibers;
30. central regions of the fiber tows saturated with an uncured elastomer;
31. a hole in the disc to accommodate stabilizing pegs;
32. the stabilizing peg extending from either the deep (shown) or superficial membrane (7, 8)
33. ends of the tows;
34. a strip of uncured elastomer;
35. a fiber-matrix composite layup;
36. a prosthetic anchor;
37. a geometric molded or machined master replicating a geometry of the central layer (1);
38. flanges to guide the fiber tows;
39. radial carbon or glass fibers in a composite layup;
40. diagonal 'a' fibers in the composite layup;
41. diagonal 'b' fibers in the composite layup;
42. a fiber composite envelope;
43. a clasp for holding the envelope (42) during fiber insertion;
44. a rim joining outer and inner laminae of the envelope (42);
45. a flange to hold the envelope laminae apart during fiber insertion;
46. a bone;
47. fixation screws;
48. a stress-distributing metal plate;
49. a mechanical energy converter surface configured to be anchored to the coupled fibers by the prosthetic anchor (36);
50. a frontal bone;
51. an olecranon of an ulna;
70. a substrate element;
71. adjustment screws;
72. threaded holes;
73. adjustment ridges;
74. adjustment grooves;
75. a fastener;
76. adjustment pegs;
77. adjustment sockets;
78. partial envelopes;
79. a middle region of a medial portion;
80. a elongated tension element;
81. a muscle insertion element;
82. a bundle of filaments or fibers;
83. a filament;
84. a needle; and
85. a muscle.

The prosthetic anchor (36) of the present invention is configured to be anchored to a hard structure, such as a prosthetic device or a bone, for minimizing material stress concentration that is otherwise inherent to such anchoring. The anchor (36) is further configured to minimize a height of the profile of the structure beyond the surface of that hard structure. As described in greater detail below, the prosthetic anchor includes an implantable, flexible, force-transmitting fiber-based tissue coupler, a central layer with fibers, and to methods of fabricating and using the same to a relatively rigid structure. The structure may be natural or prosthetic, in a human or animal body, with improved stress distribution when used as a fixed tension member, such a tendon or ligament. The anchor may be useful in cardiac, plastic, reconstructive, and/or orthopaedic surgical applications.

To this end, the prosthetic anchor defines a thin wafer-like device including a central layer that incorporates, or embeds, multiple bundles of fibers of a tension member, e.g. a natural or artificial tendon, to form a matrix. The central layer may be constructed from an elastomeric or other polymeric material. The fibers are packed closely and concentric therein but permit permeation and interstitial distribution of the matrix. In one pattern, the fibers are generally horseshoe in shape. Opposing ends of each fiber exits the central layer from generally same side or edge of the central layer and may be attached to the natural or artificial surface by methods that are commonly known to those of ordinary skill in the art. Harder and thinner surface membranes, such as those constructed from carbon-fiber/epoxy, glass-fiber/epoxy, or sheets of biocompatible metals may be used to cover, or sandwich, one or both faces of the central layer, to provide variable flexibility. The degree of flexibility may be dependent on thickness of the overall structure and the selected materials for the surface membranes and the central matrix layer. Generally, regions near the concentric path of the fibers will not contain fibers and may include any combination of the layers.

Figure 3:
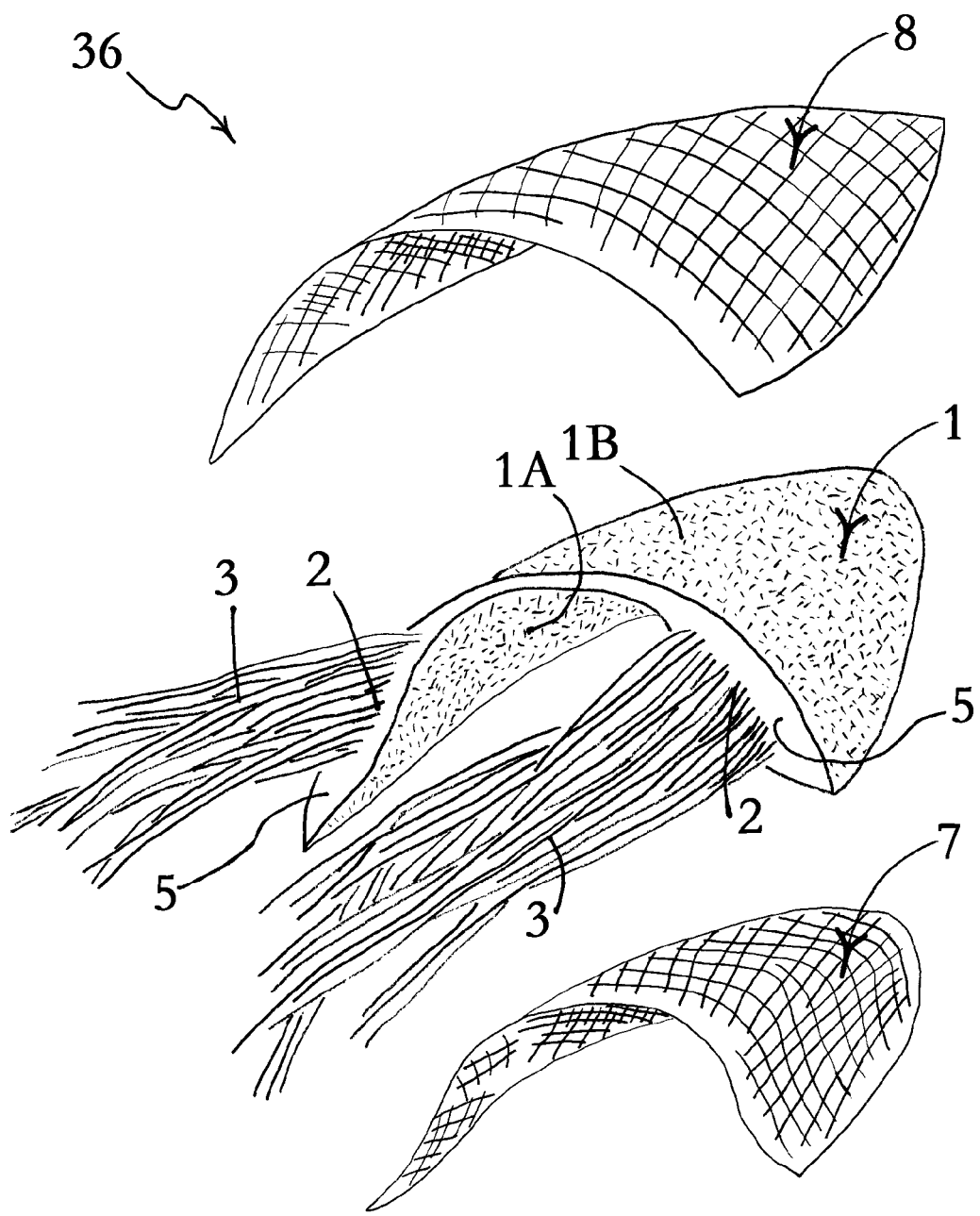
FIG. 3 is an exploded view of a prosthetic anchor in accordance with another embodiment of the present invention and including a central layer with thin semi-rigid surface membranes on either side.

As shown in FIGS. 1-3, the prosthetic anchor (36) generally includes three layers: (a) a central layer (1) of wafer-like structure, defining a matrix, through which embedded fibers (2) pass in defined pathways (4). Examples of materials for constructing the central layer (1) include polymers, such as elastomeric material (e.g. silicone rubber and polyurethane). The fibers (2) may include natural material (e.g. human and/or animal tendons or ligaments) and/or synthetic materials such as polyester for defining a tendon or ligament; (b) a 'deep' surface membrane (7) configured to interface with a hard structure, such as by being anchored to, for example, a prosthesis, a bone, or other hard tissue. Examples of materials for constructing the membrane (7) are titanium alloy or other metal, fiber (e.g., carbon, glass) or epoxy composites, and combinations of metals and fiber composites; and (c) a 'superficial' surface membrane (8) which interfaces with an adjacent tissue and may be configured to adhere or not to adhere to that tissue. Examples of materials for constructing the membrane (8) are titanium alloy or other metal, fiber (e.g., carbon, glass) or epoxy composites, and combinations of metals and fiber composites.

The surface membranes may be smooth or textured so as to discourage or encourage tissue adherence, respectively. The side of each membrane that interfaces with the central layer may or may not be roughened or textured to achieve a mechanical bond with the matrix layer. Additionally, or alternatively, various adhesives may be applied to secure the surface membranes to the matrix layer. Since the rigid structure, whether it is a hard tissue or a rigid prosthesis may be moveable relative to surrounding or adjacent soft tissues, the peripheral margins of the anchor may be generally tapered to a thin edge. The anchor may also be adapted for mechanical fixation to the natural or prosthetic rigid structure and, more specifically, may include one or more of simple holes for screws, anchors, integrated pegs, and/or hooks.

The deep and/or the superficial surface membranes (7, 8) may have one or more projections, such as posts or needles, described in detail below, that extend through openings in the elastomeric central layer (1) to provide counter force to the fibers (2) as the fibers (2) are tensed. In addition, it should be understood that the surface membranes (7, 8) are optional insofar as the central layer (1) may be adapted to function alone or with one surface membrane (7 or 8), thereby defining the prosthetic anchor (36).

With further reference to FIGS. 1-3, the embedded fibers (2) traverse the central layer (1). The fiber bundles (3) enter and exit the wafer-like layer (1) generally on the same side thereof. Within the central layer (1) the embedded fibers (2) traverse concentric substantially parabolic pathways (4). The elastomeric material near an edge (5) of the central layer (1), at which fiber bundles (3) enter and exit, may be thicker than in other regions of the central layer (1) so as to lessen and distribute local stress concentration effected by tensioning of the fibers (2). Adjacent the concentric fiber pathways (4), there may be an opening (6), which may serve to accommodate either a post or projection (32) (See FIG. 13b and FIG. 13c) during fabrication, a compression member providing counter-force when tension is applied to the fibers (2) or both. As best shown in FIGS. 2a-2d and 3, the semi-rigid surface membranes (7, 8) envelop the elastomeric layer (1) and preferably adhere thereto.

Figure 4:
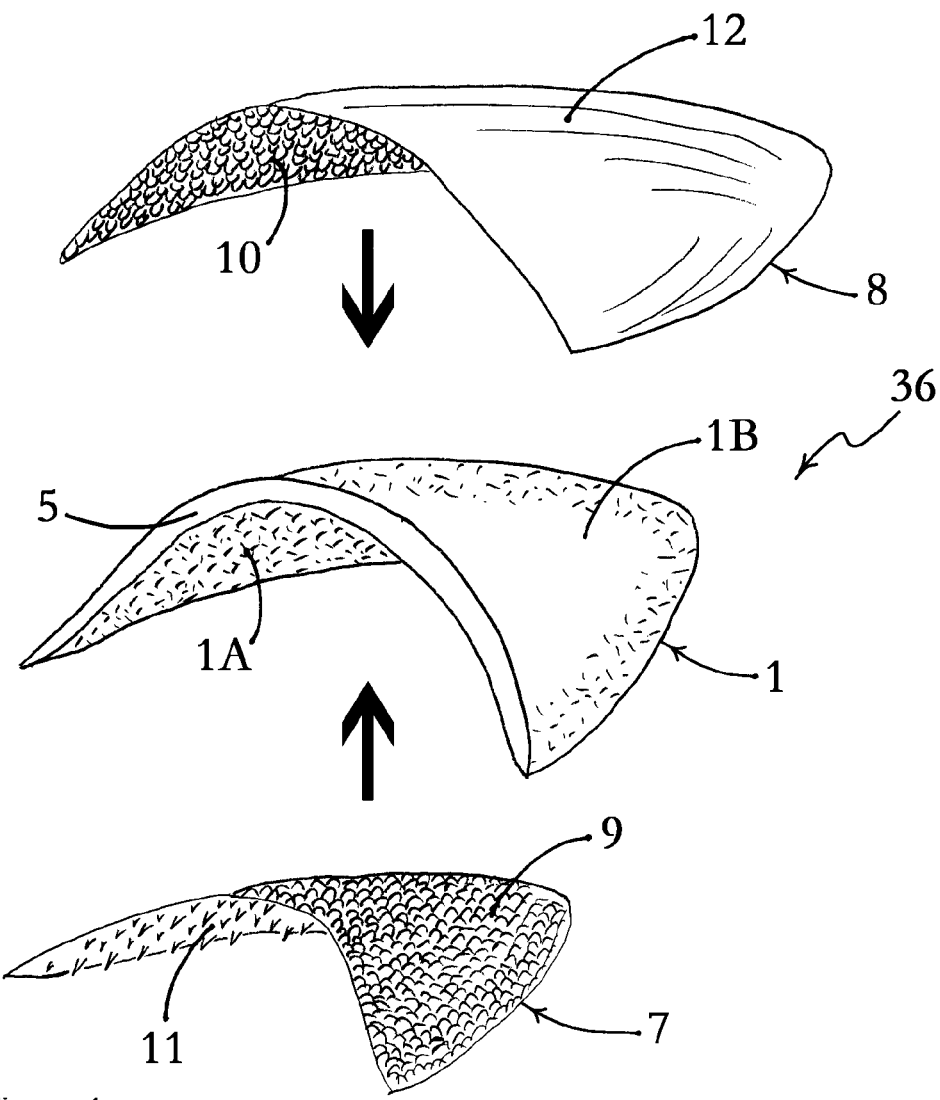
FIG. 4 is an exploded view of a prosthetic anchor, similar to that of FIG. 3, and in accordance with another embodiment of the present invention.

FIG. 4 shows another embodiment of the device (36) of the present invention (fibers not shown for simplicity) wherein the surfaces (9, 10, 11, 12) are altered. More specifically, those surfaces (9, 10) facing central layer (1) are textured to adhere to the matrix material of the central layer (1). The outer surface (11) of the deep surface membrane (7) is spiked, which might be chosen on one non-limiting example of surface alteration to facilitate fixation to bone. The spiked surface may alternatively incorporate textured metal plates, barbs, or meshes in that surface (11). The outer surface (12) of the superficial surface membrane (8) facing tissue is polished and smoothed to generate a sliding, bursa-like interface.

FIGS. 5 through 23 illustrate methods of fabricating the prosthetic anchor (36) in accordance with one or more embodiments of the present invention.

Figure 5:
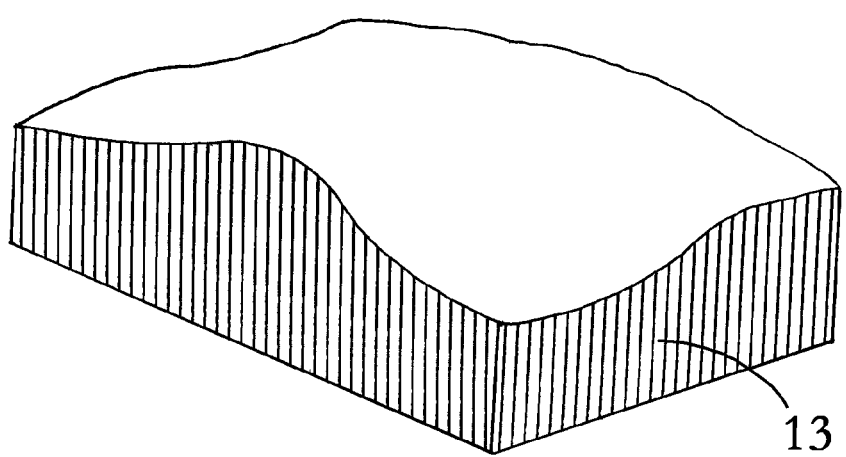
FIGS. 5 through 23 illustrate methods of fabricating a prosthetic anchor in accordance with various embodiments of the present invention.

FIG. 5 shows step (a) wherein a block surface (13) of polished steel, polished ceramic, glass-filled epoxy polyester resin, or other material is produced, e.g. machined, molded, or cast, as appropriate, in the form of the surface to which the device (36) is to be attached. Alternatively, the actual target anchoring surface may be used, such as the mechanical interfacing part of a cardiac prosthesis, an excised anatomically typical bone with appropriate lacquering, or other surface treatment.

Figure 6:
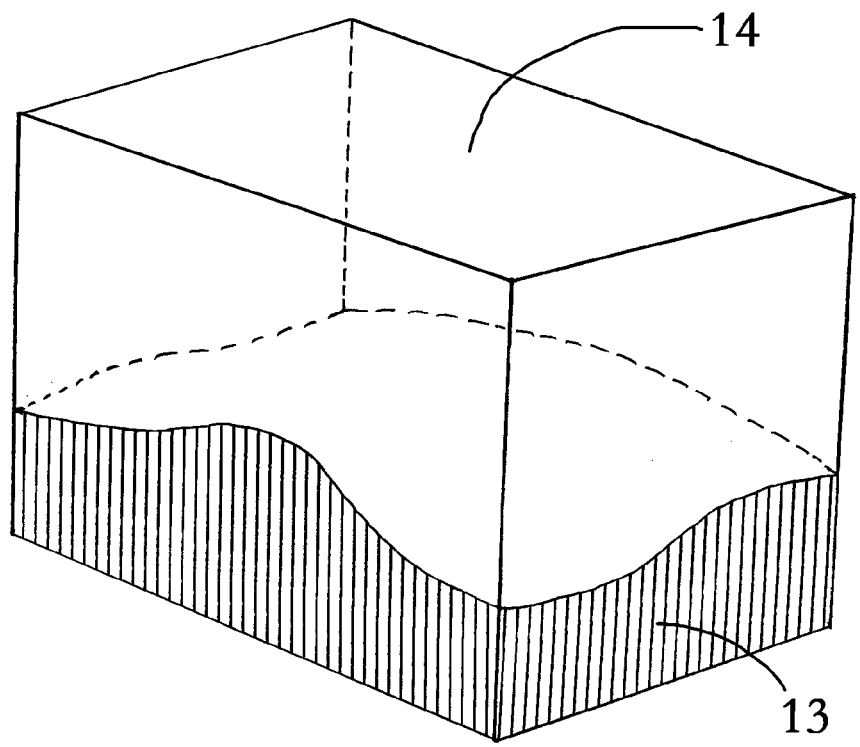
Figure 7:
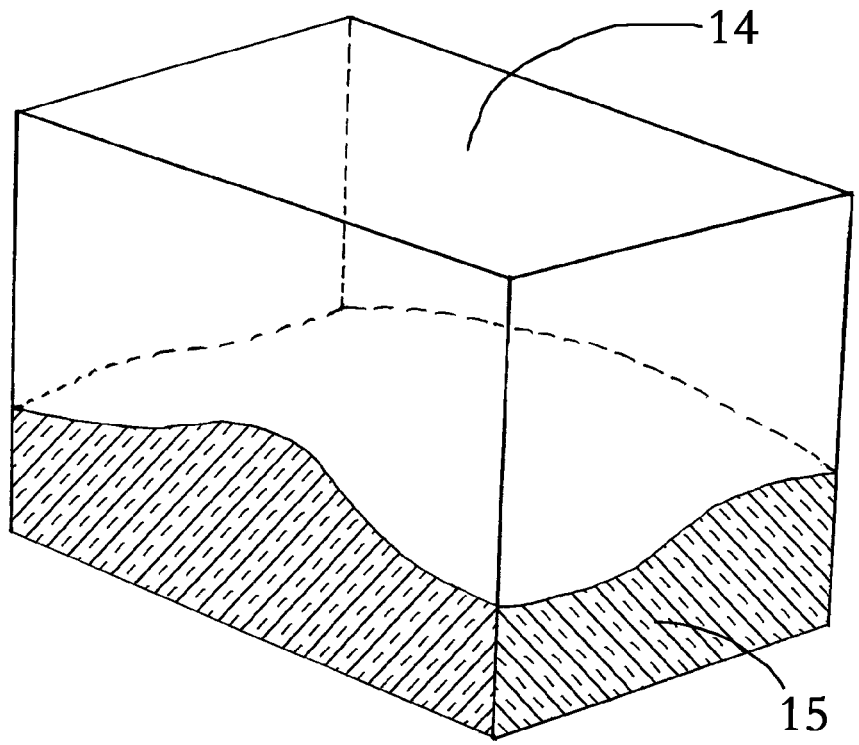

FIG. 6 shows step (b) wherein the surface, or surface replica (13), is used to form a mold (14) of a soft elastomeric material such as a polyurethane or silicone rubber. FIG. 7 shows step (c) wherein a hard mating surface (15), such as a glass-filled epoxy polyester resin or other material, is cast. This mating surface called "fabrication part B" (15) is a replica of the applicable surface of the surface replica (13).

Figure 8:
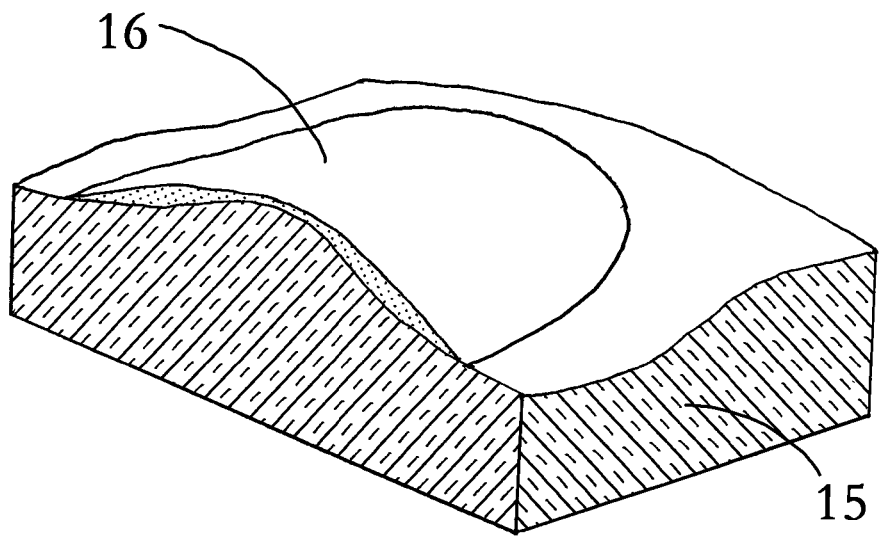
Figure 9:
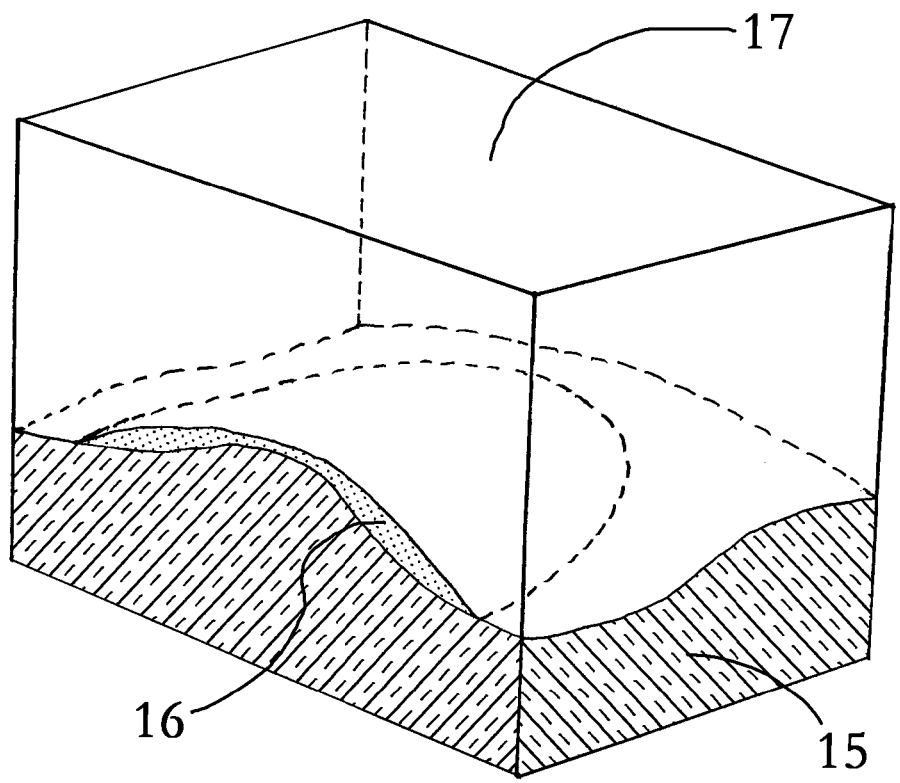

FIG. 8 shows step (d) wherein a clay wafer (16), or a wafer of curable clay-like modeling polymer, having a geometry that mimics the desired geometry of the anchor (36) is formed on the surface of fabrication part B (15). The wafer (16) is cured or hardened to produce "fabrication part C." FIG. 9 shows step (e) wherein, after liberally applying one or more mold-release agent(s), a hard outer cast called "fabrication part D" (17) is formed to mate with the fabrication parts B (15) and C (16) assembly.

Figure 10A:
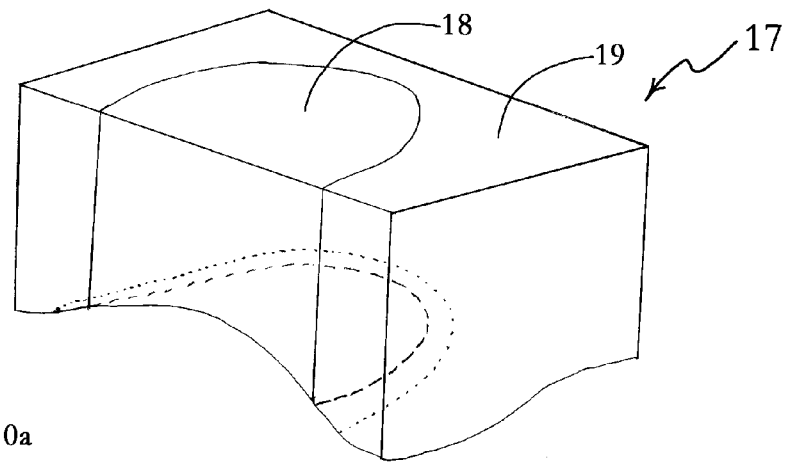
Figure 10B:
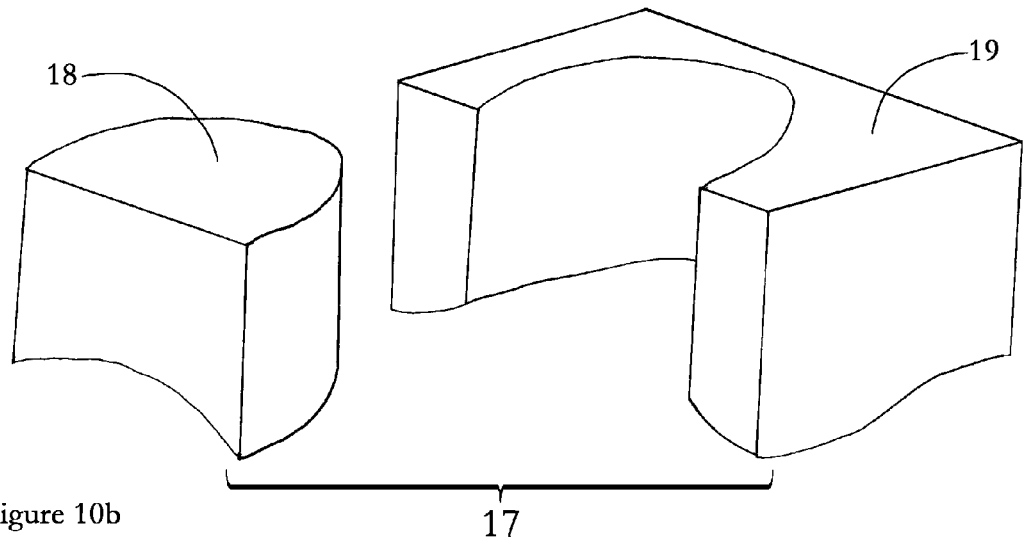
Figure 11:
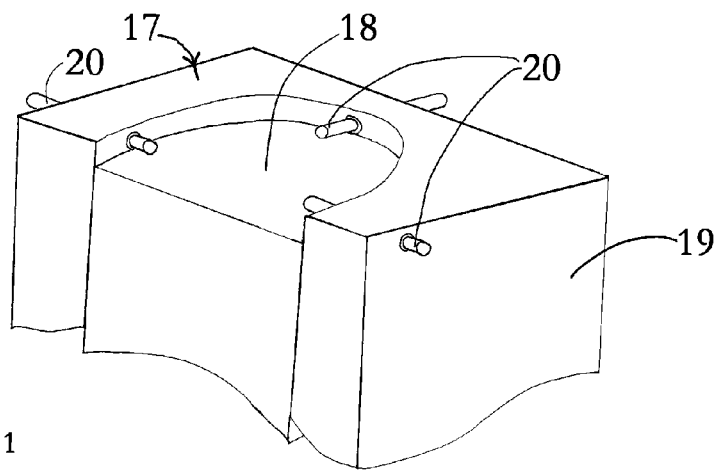

FIG. 10a and FIG. 10b show step (f) that includes using a scroll saw, a wire cutter, a laser beam, or other tool to cut a short distance, generally 2-3 mm, inside the Fabrication part D (17) and concentric to the margin of Fabrication part C (16) to form an inner section (18) and an outer section (19). FIG. 11 shows step (g) wherein the Fabrication part F (19) is offset from its original position on Fabrication part E (18) by a short distance, approximately the thickness of a diameter of a fiber tow (28), to facilitate step (m) (See FIG. 17) described below. The distance may be, generally, 1 to 3 mm, and the Fabrication part F (19) is held in place by a removable pin (20) or other means.

FIGS. 12a-12g illustrate step (h) wherein a multilayer fiber/polymer composite layup is formed between the mating surfaces of Fabrication parts A and B (14, 15). The composite layup may be constructed with carbon-fiber/epoxy and glass fiber/epoxy, by either manually saturating or utilizing pre-impregnated sheets and curing the layup under compression to form the deep semi-rigid surface membrane (7). A least a portion of either surface of the deep or superficial surface membranes (7, 8) may be a smooth surface (21). One or more strips or plates of textured or sintered metal plates (not shown), metal mesh (22), or other materials designed for adhering to the bony or other mounting surface may be incorporated between the composite layup and the Fabrication part A (14), and underlying at least a portion of that surface. The degree of metallic or other material underlayment is dependent on design goals, particularly desired regional flexibility or rigidity.

Figure 12A:
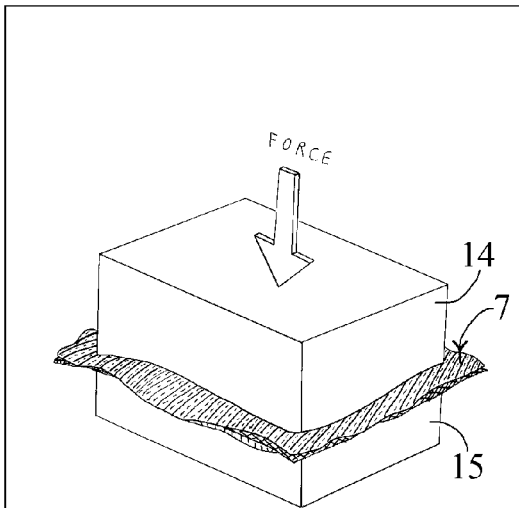
Figure 12B:
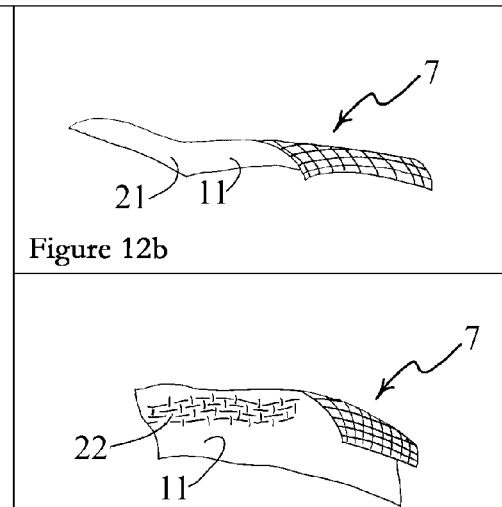
Figure 12C:
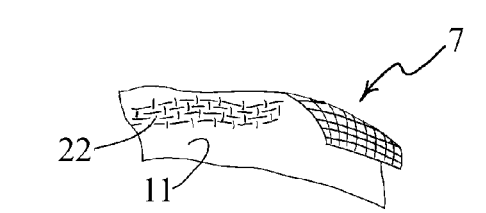
Figure 12D:
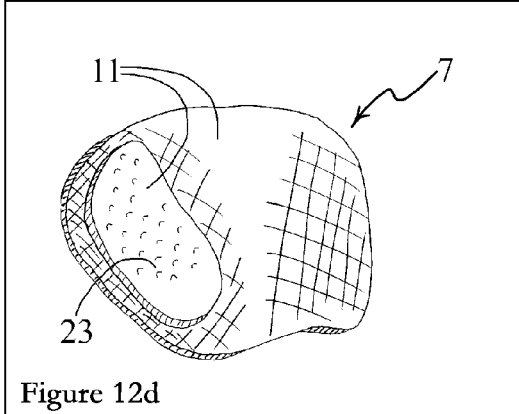
Figure 12E:
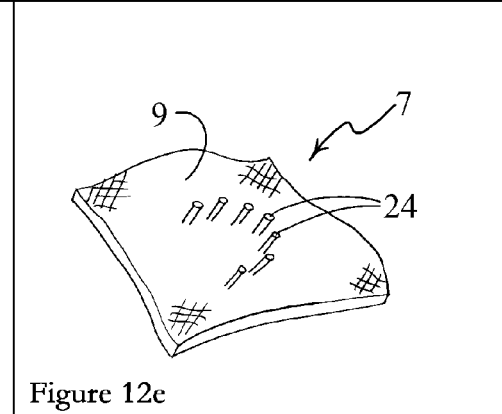
Figure 12F:
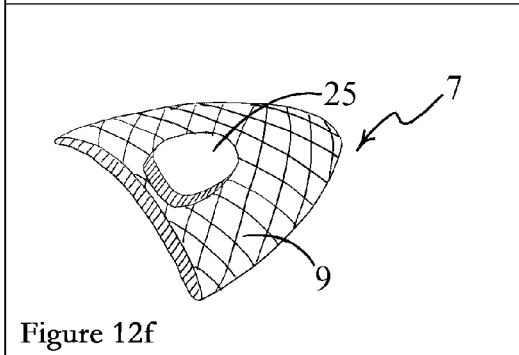
Figure 12G:
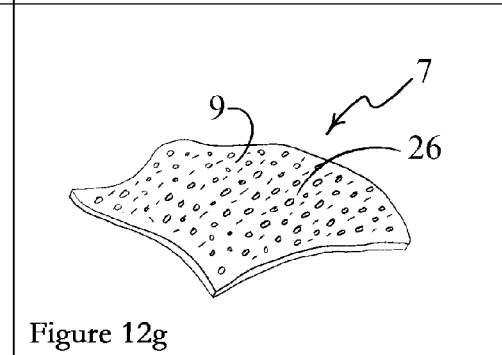

Specifically, FIG. 12a shows the process of forming the composite layer under pressure, while FIGS. 12b, 12c, and 12d show possible variations in the outer or deep surface of the deep layer surface membrane (7) according to various embodiments of the present invention. That this, the surface may be smooth (21) as in FIG. 12b, incorporating a metal mesh (22) as in FIG. 12c, and/or a textured metal plate (23) as in FIG. 12d. FIGS. 12e, 12f and 12g show still other superficial surface of the deep layer (7). FIG. 12e shows a composite layer with short needle-like projections (24) in the superficial surface of the deep surface membrane (7), which may be formed by drilling appropriate holes in the mating surface of Fabrication Part B (15) or by adding metallic or other projections or 'tacks' to Fabrication Part A (14) prior to the layup. The needle-like projections (24) are shown in an array chosen to support the fiber placement procedure described below in FIG. 17, step (m). FIG. 12f illustrates a deep composite surface membrane (7) with a peg-like central plateau (25) that serves the same purposes of the needle-like projections (24) of FIG. 12e. Finally, FIG. 12g shows a roughened, textured (26) portion of superficial surface of the deep composite membrane such as may be affected, for example, by preliminary mechanical pitting of Fabrication part B (15). Features 22 through 26 may be used in any combination or used alone.

FIG. 13a shows step (i) wherein a generally parabolic disc (27) of porous biocompatible material is saturated in an uncured silicone rubber or other elastomeric resin, positioned on the deep surface membrane (7), and aligned with projections (24) of the type illustrated in FIG. 12e. The porous biocompatible material may be constructed from a polyester fabric, in one or more layers. Alternately, as shown in FIG. 13b and FIG. 13c, a hole (31) in the fabric or other disc material (27) can be configured to fit about one or more peg-like plateaus or projections (32) from the superficial surface of the deep surface membrane (7). The fabric disc (27) is separated from the deep surface membrane (7) in the right of the two drawings for clarity, and in operable position on the left.

Figure 13D:
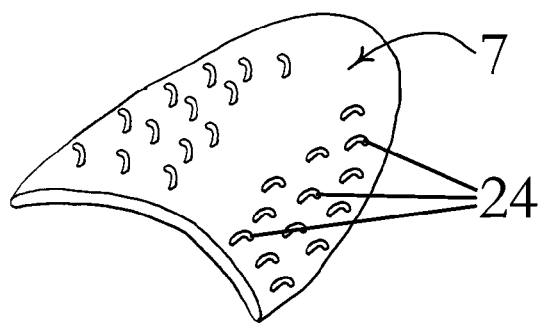

FIG. 13d shows a series of projections (24), which may or may not be hook-like in configuration, that extend superficially from the deep surface membrane (7) to stabilize and support various concentric groups of the fibers during casting of the fiber/elastomeric-matrix composite wafer (1). The projections (24) may be generally positioned in two or more concentric curved rows of two or more projections. For example, FIG. 13d shows three concentric rows having six, eight, and twelve projections (24), respectively.

Figure 14:
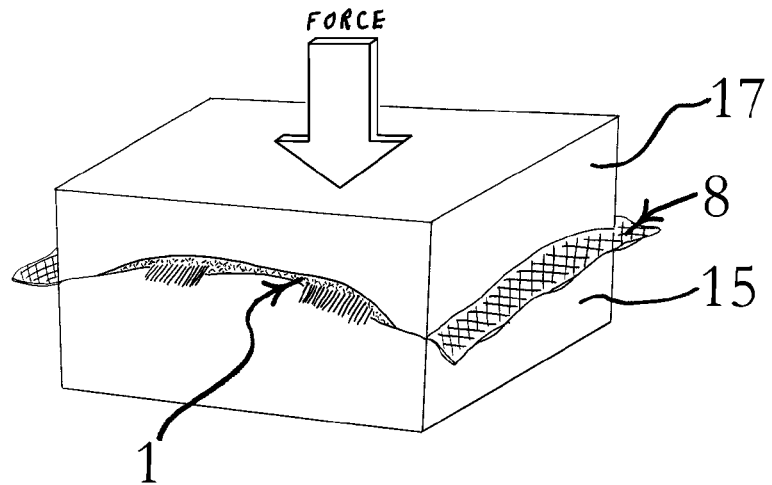
Figure 15:
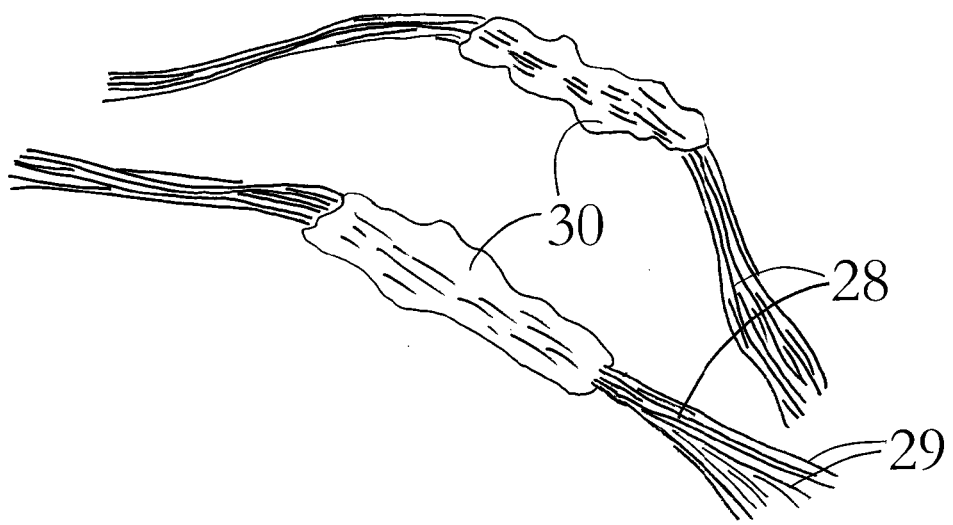

FIG. 14 shows step (j) wherein the uncut Fabrication Part D (17) and the Fabrication Part B (15) are held together in compression on opposite sides of the central layer (1) and cured to form the superficial surface membrane (8). FIG. 15 shows step (k) wherein bundles or tows (28) of the individual coupler fibers (29) are saturated with uncured elastomer resin in their central regions (30). The bundles may include several dozen to several thousand fibers constructed from a polymer, such as polyester, having a diameter that generally ranges from about 6 microns to about 20 microns.

The next steps describe three methods for stabilizing fibers and embedding them within the elastomer of the central wafer-like layer (1) according to various embodiments of the present invention.

FIGS. 16-20 (steps l through p), as further described below, illustrate a method of stabilizing the fibers, pending elastomeric matrix curing, by opposed rigid restraining surfaces. More specifically, the figures illustrate one method of insinuating bundles (28) between two restraining surfaces and sequentially tensing each bundle against a concentrically-positioned bundle, wherein the distance separating the two restraining surfaces determines how thick or thin (i.e., how concentrated or spread out) the fibers are at a particular location. In this method, the innermost fiber bundle is supported by a generally parabolic disc of porous material, one or more projections (peg or needle-like) extending from at least one of the surfaces, or both.

Figure 16:
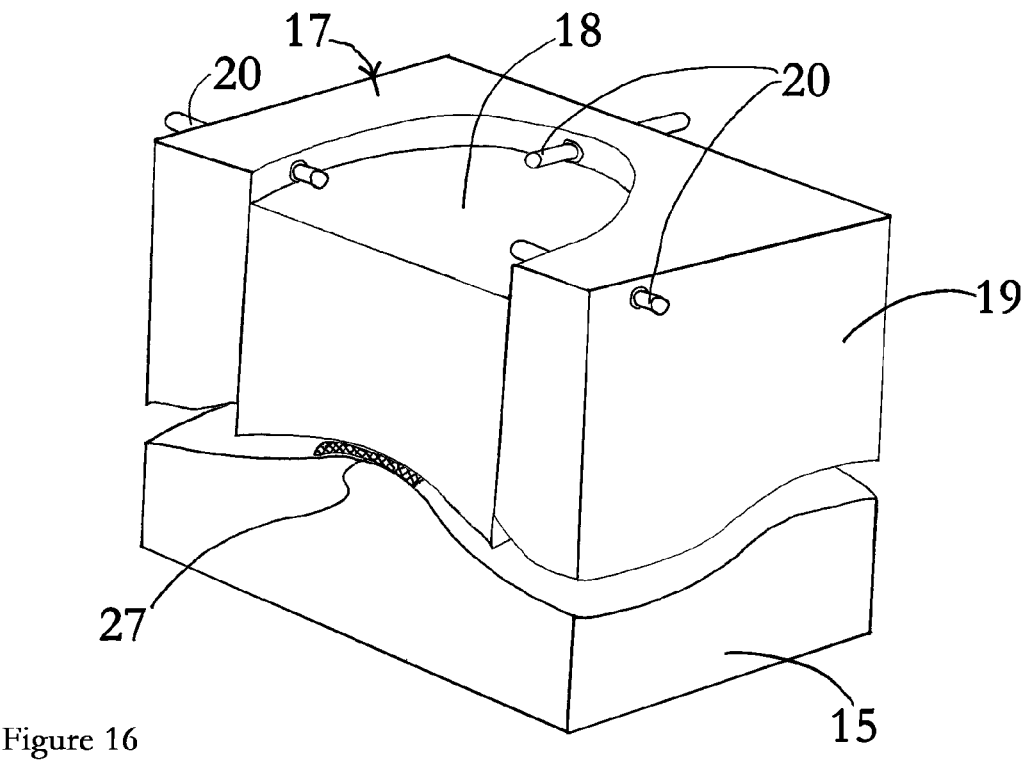
Figure 17:
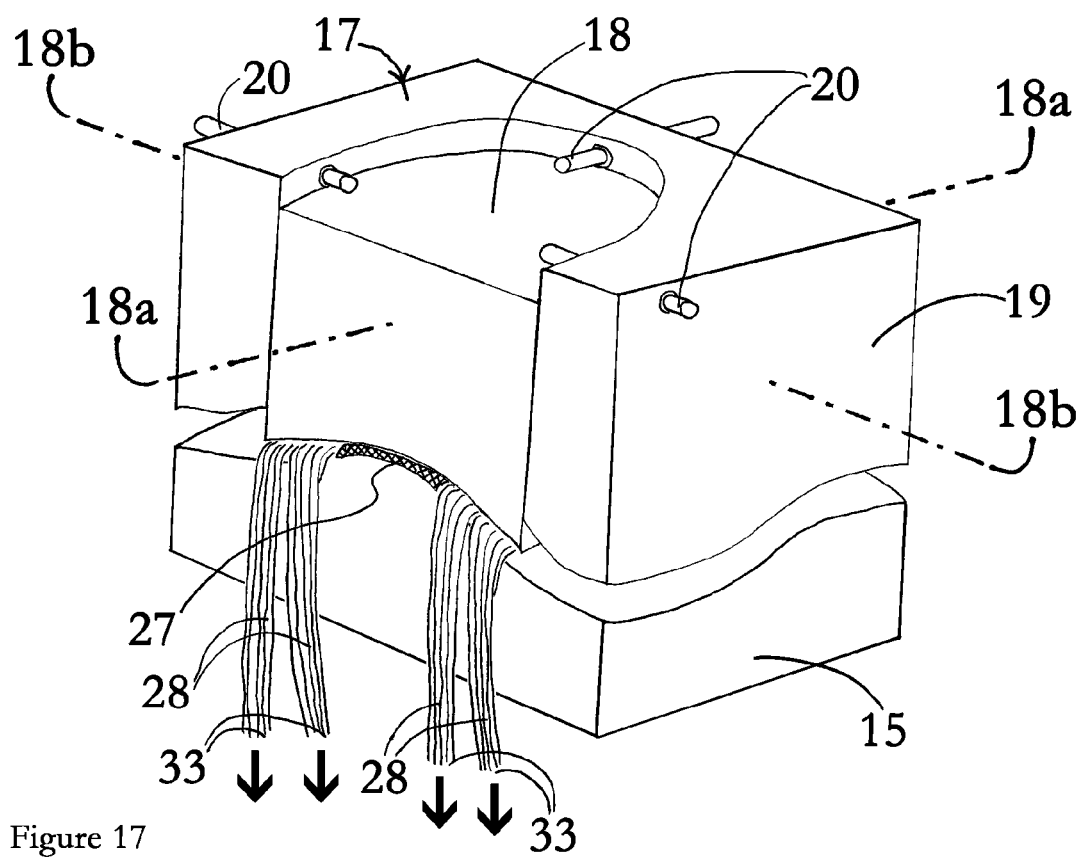

FIG. 16 shows step (l) for fabricating the device (36). More particularly, the assembled fabrication parts E (18) and F (19) (as in step g) are placed on the surface of the fabric disc (27) and rigidly clamped so that a space that is approximately the thickness of a diameter of a fiber tow (28) remains between parts F (19) and B (15). FIG. 17 shows step (m) wherein each of the one or more tows or bundles (28) of fibers, with tension applied on either end (33), is insinuated between the margins of fabrication parts F (19) and B (15). The tows or bundles (28) of fibers are maneuvered centrally by maintenance of that tension until each tow or bundle (28) lies between fabrication parts E (18) and B (15). The tows or bundles (28) are sequentially held securely against, first, the fabric disc (27), and then against prior bundles, progressing concentrically outward.

Figure 18A:
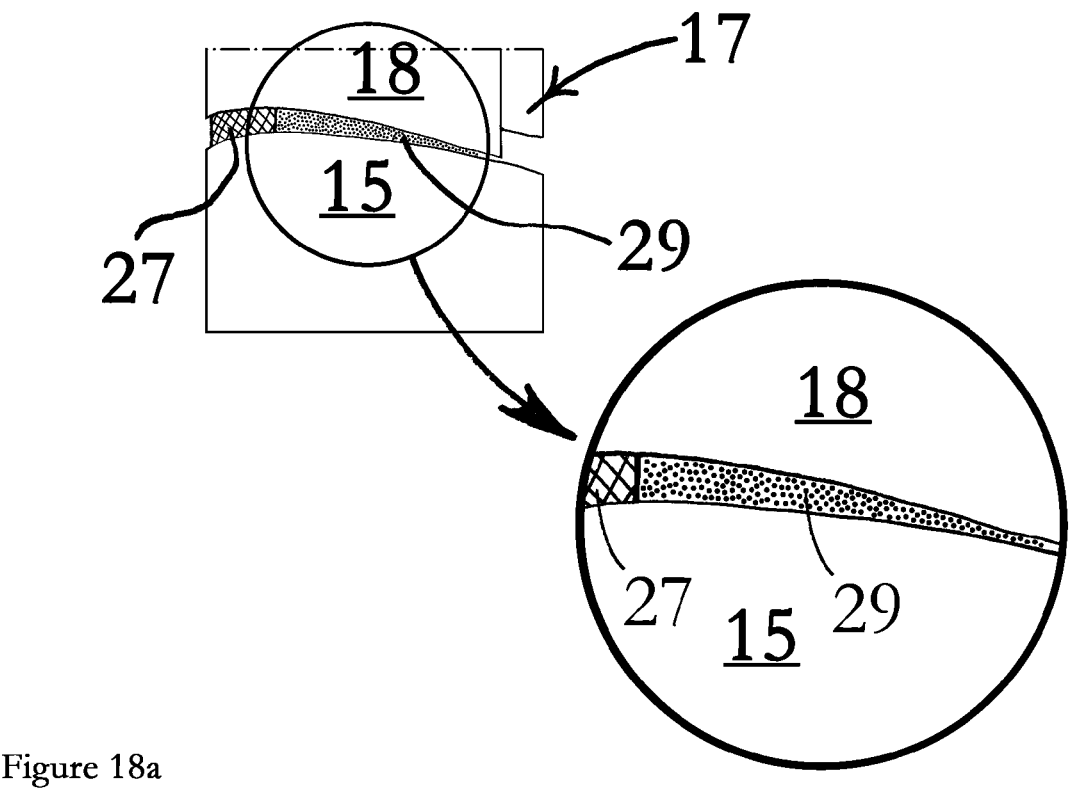
Figure 18B:
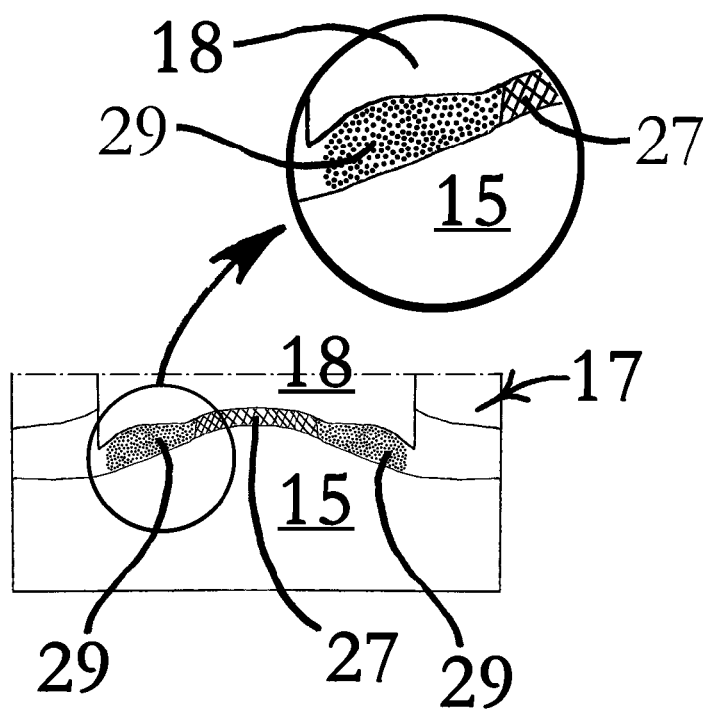

FIG. 18a and FIG. 18b are cross-sectional views taken respectively along line 18a-18a and line 18b-18b of FIG. 17 and show step (n) wherein the varying thickness of the space between fabrication parts E (18) and B (15), as determined by the varying thickness of Fabrication part C (16) used to mold part E (18), determines the varying thickness of the fiber layer as it progresses radially away from the central disc (27). The fiber layer may progress differently in terms of distance covered per number of fibers (29), at different points around the central disc (27), and is dependent on the varying thickness profile. As shown, the center of the approximately cylindrical wrap (generally 180° round) is irregular in that the wrap is thinner and wider centrally than at the sides.

Figure 19:
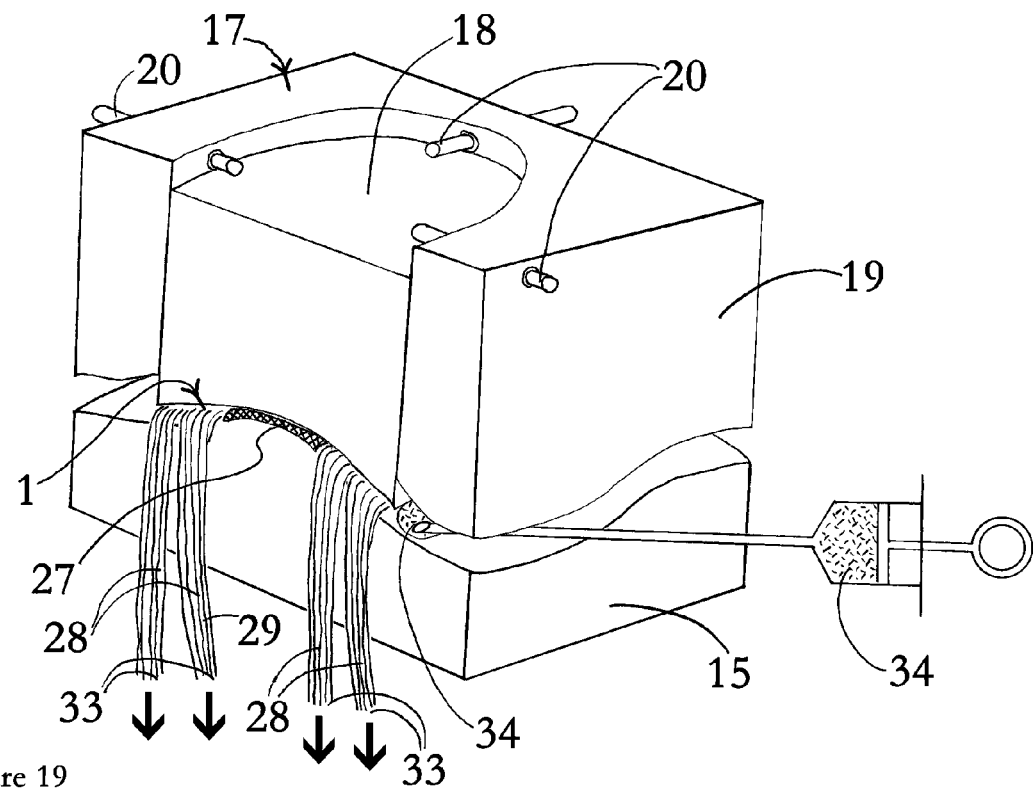
Figure 20:
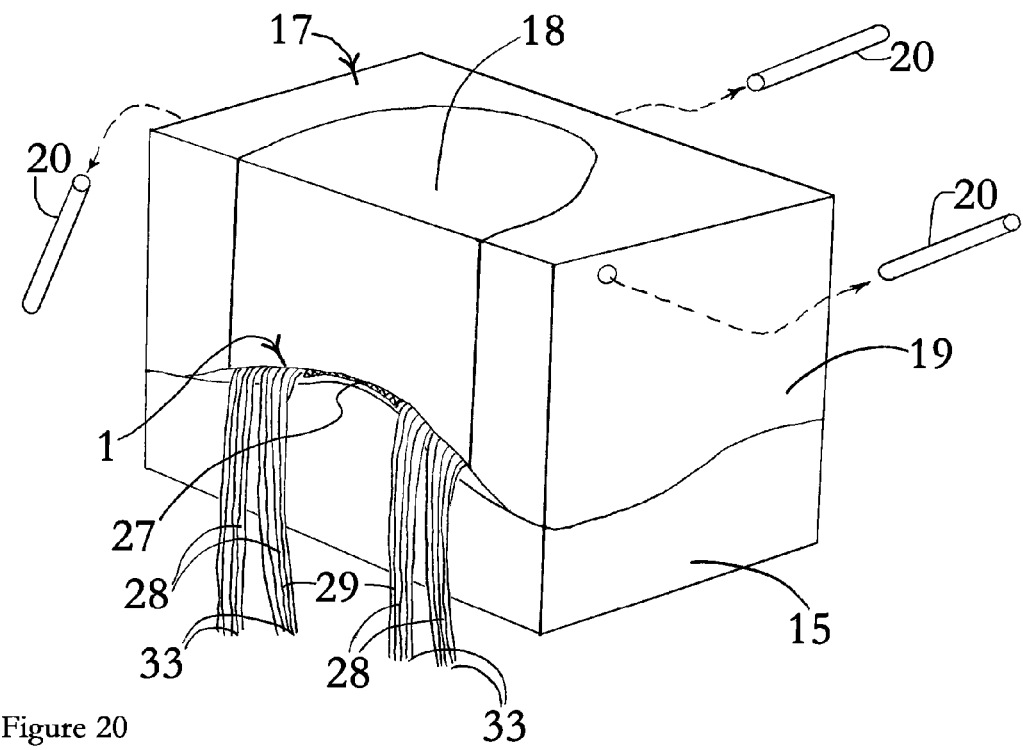

FIG. 19 shows step (o). When the desired number of fibers (29) has been placed, and either end (33) of each bundle (28) of fibers is secured by tension, the strip of uncured elastomer (34) is applied, peripherally, to form the central layer (1). FIG. 20 shows step (p) wherein the temporary securing pins (20) are removed to allow the Fabrication Part F (19) to be advanced on to the Fabrication Part E (18) until it contacts and is compressed against the Fabrication Part B (15). Excessive uncured elastomer is expressed and the elastomer is cured to form the central layer (1).

Figure 21:
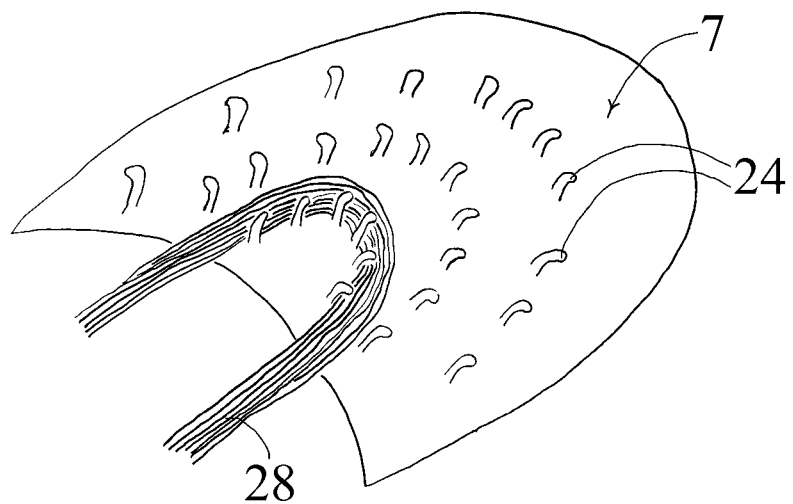
Figure 22:
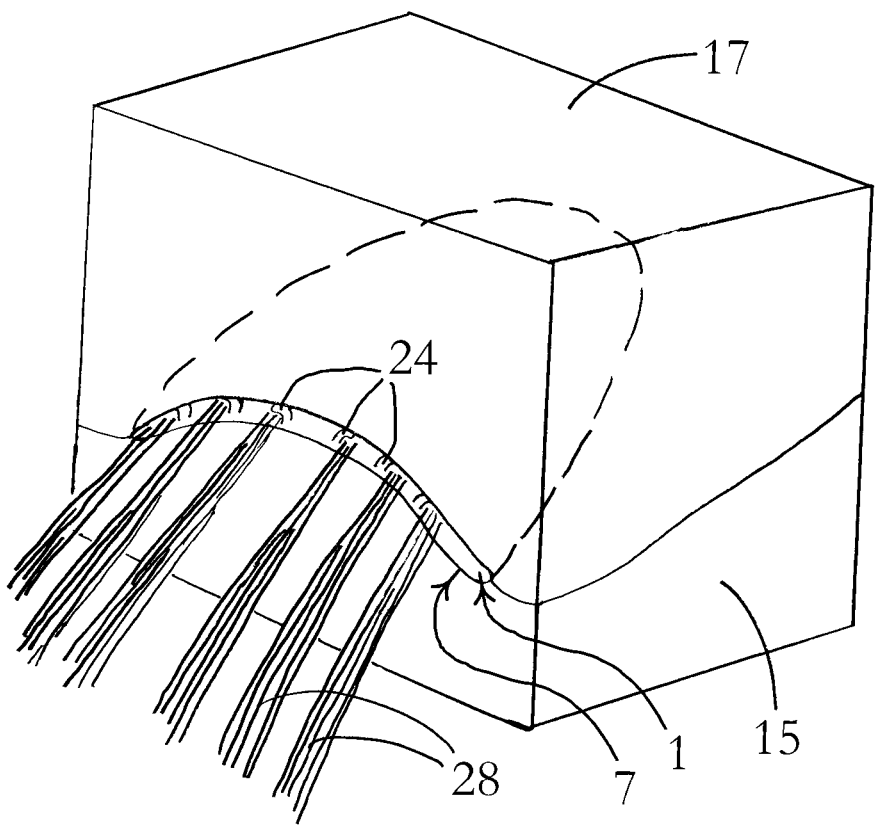

FIGS. 21 and 22 (steps q and r) show another method of stabilizing fibers in accordance with another embodiment of the present invention. Herein, one or both of the enveloping membranes (7, 8) include needle-like projections (24) that, as shown, may be arranged into two or more concentric curved rows. The needle-like projections (24) may be hook-shaped as it extends from one of the enveloping membranes (7) to the other. The membrane may be constructed from a range of metallic, fiber-matrix composite, or other materials.

Figure 23:
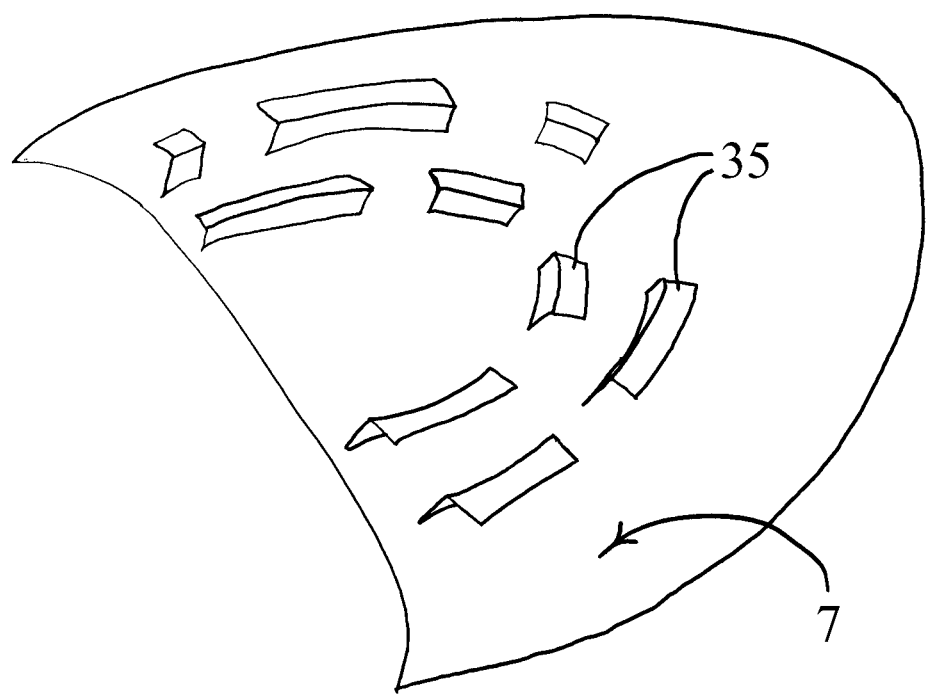

Specifically, in step (q), FIG. 21 illustrates each elastomer-saturated bundle, or group of one or more bundles (28), placed around one concentric row of hook-like extensions (24). The bundles are placed, one at a time, progressing outwardly, under tension until all bundles are in place. Accordingly, it should be understood that the extensions (24) may be provided on one or both of the surface membranes (7, 8). Next, in step (r), as shown in FIG. 22, the uncut part (17) or the "Fabrication part D" that is positioned on the surface of projections (24) and the bundles (28). Pressure is applied and the central layer (1) may be cured in manner that is similar to step (p) of FIG. 20. FIG. 23 shows step (s), another variation of step (q) in which the projections extending from membrane (7) or membrane (8) include one or more flanges (35) configured to support successive concentric bundles of fibers.

Dependent upon which manufacture method has been employed, the appropriate surface membrane(s) (7, 8), such as a carbon-fiber composite or glass-fiber composite, may be applied (e.g. adhesively) to the elastomeric central layer (1) following curing. In multiple laminae the membranes (7,8) may be applied to the opposite surface(s) of the central layer (1) to form the prosthetic anchor (36). It should be understood that the surface membranes (7, 8) may be optional insofar as the central layer (1) may be provided alone (i.e. without the surface membranes (7, 8)) or with only one surface membrane (7 or 8), thereby defining the prosthetic anchor (36). Accordingly, it should be understood that the material of the central layer (1) may be modified to provide the desired flexibility or rigidity and optionally, or additionally, include a suitable polymer and carbon-fiber composite or glass-fiber composite with a matrix, such as epoxy.

Figure 24:
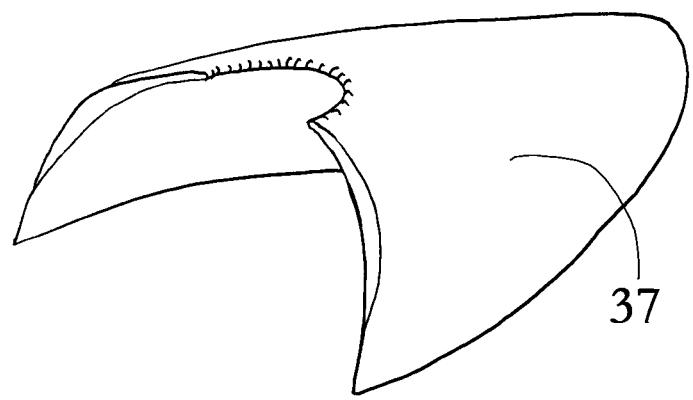
FIG. 24 is a perspective view of a bloc replica for fabricating a central layer in accordance with one embodiment of the present invention.
Figure 25:
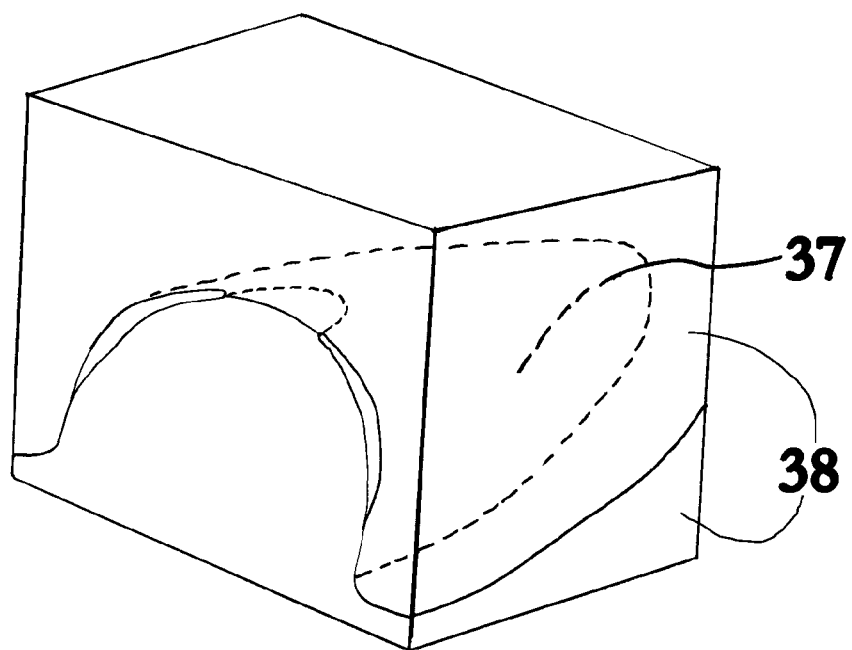
FIG. 25 is a perspective view of a silicone mold for fabricating the bloc replica of FIG. 24 in accordance with one embodiment of the present invention.

FIGS. 24 and 25 show yet another method of manufacture in accordance with another embodiment of the present invention. Therein, an envelope (42) of fiber-matrix composite, such as carbon-fiber/epoxy, may be preformed and the fibers inserted with an uncured elastomer through an open margin of the envelope. The assembly defining the prosthetic anchor (36) may then be is fixed to the bone or prosthesis with screws or other means, which also fix the margins of the envelope.

Figure 26:
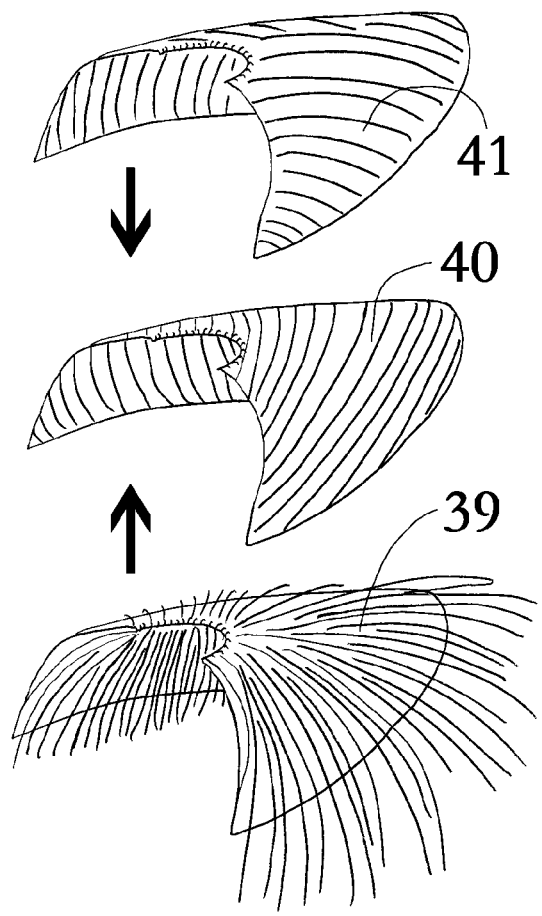
FIG. 26 is an exploded view of radial fibers having two diagonal layers in space according to another embodiment of the present invention.

More specifically, FIG. 24 shows step (aa), wherein a machined or molded bloc replica (also referred to as a master (37) of the envelope or wafer (42) is provided. FIG. 25 shows step (bb) for providing a two-part silicone mold (38) of the master (37). FIG. 26 illustrates an optional step (cc), wherein similar layers or surface membranes may be "laid up" (not shown) on the deep side of the master (37) as well. In particular, FIG. 26 shows radial fibers (39), such as carbon, glass, or other, with two diagonal layers (40, 41) in space.

Figure 27:
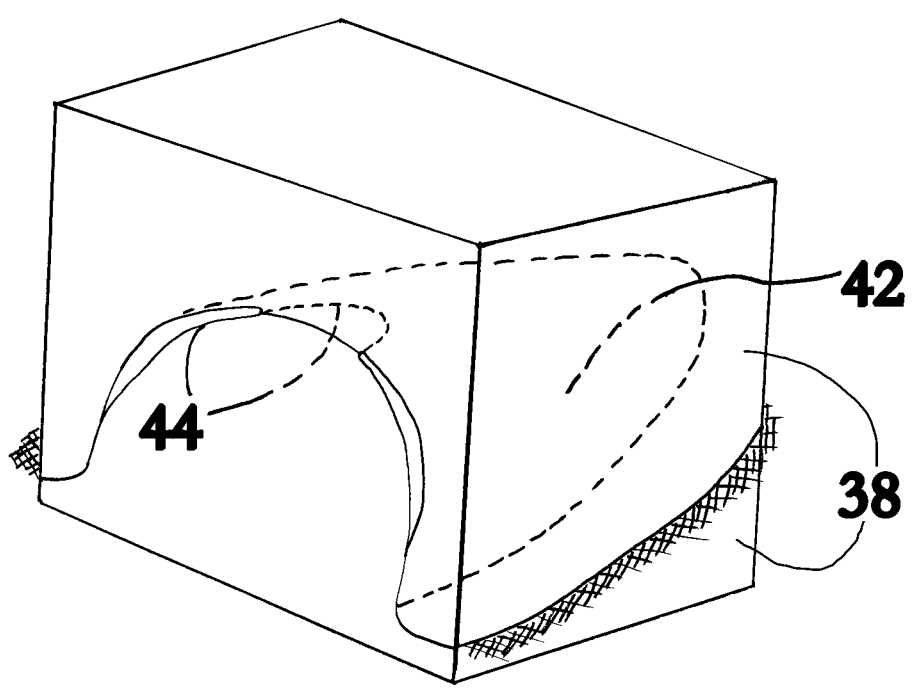
FIG. 27 illustrates a method of curing a portion of the anchor in the mold of FIG. 25 and in accordance with one embodiment of the present invention.
Figure 28A:
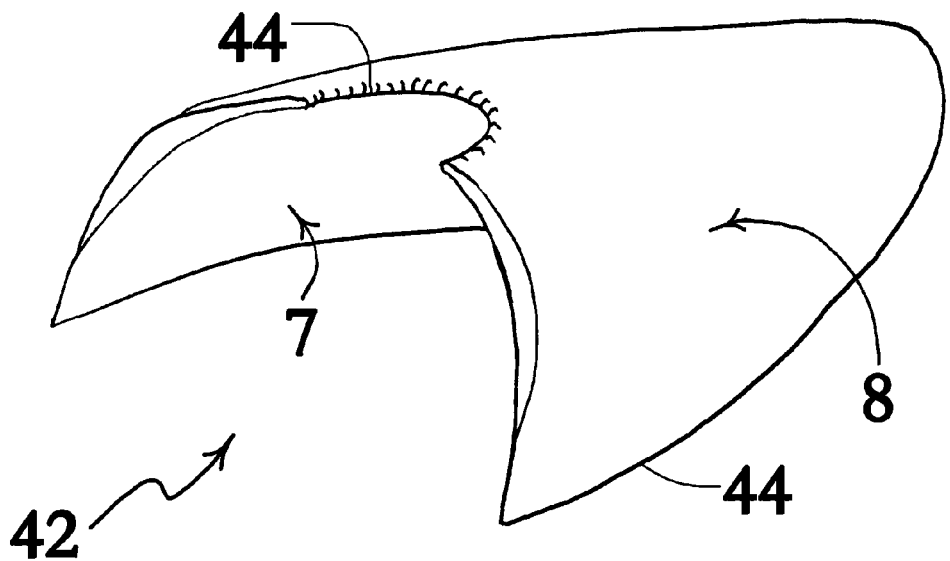
FIG. 28a and FIG. 28b illustrate a demolded, trimmed, fiber-composite envelope alone (FIG. 28a) and held in clasp (FIG. 28b) for insertion of fibers according to one embodiment of the present invention.
Figure 28B:
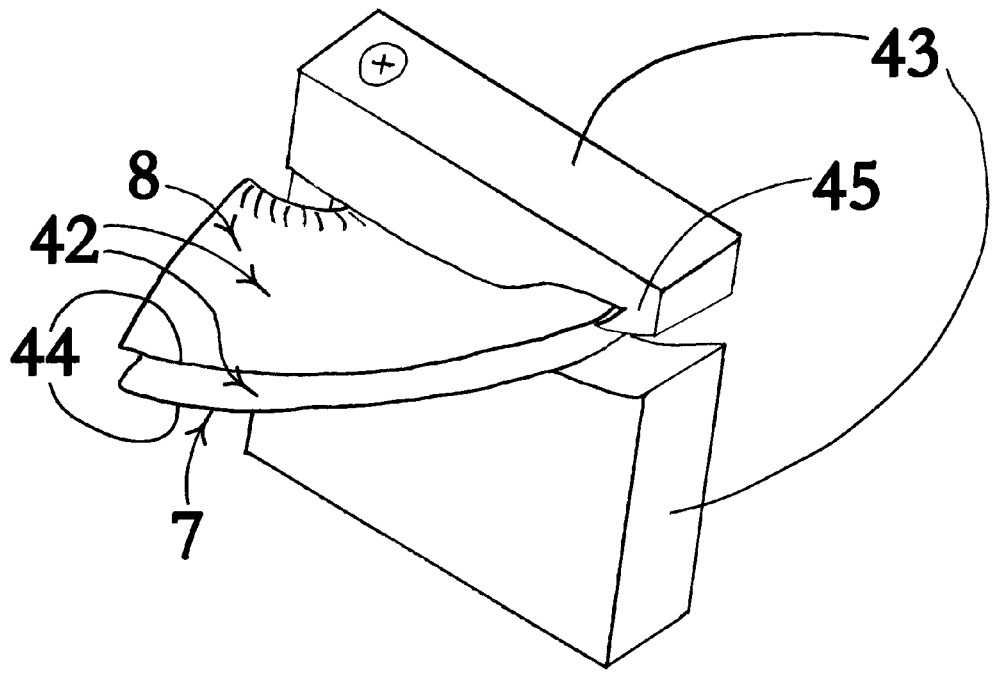
Figure 29:
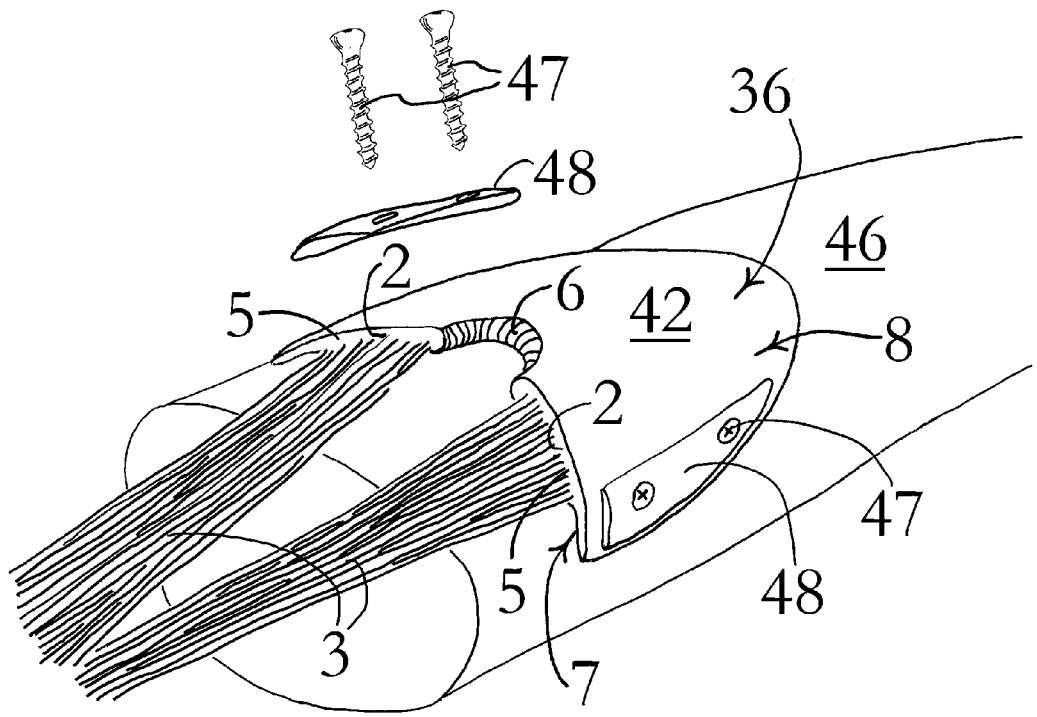
FIG. 29 shows a method of affixing a prosthetic anchor to a bone with screws and metal stress-distributing plates.

FIG. 27 illustrates step (dd) in which the mold (38) is cured to form fiber-composite envelope (42). FIG. 28a and FIG. 28b illustrate step (ee) in which the fiber-composite envelope (42) is demolded and trimmed (see FIG. 28a) and held in clasp (43) (see FIG. 28b) for insertion of the fibers. The outer and inner membranes (7, 8) of the envelope (42) are united only at the margin (44) of the parabolic shaped opening. The clasp (43) has a flange (45) to hold the envelope (42) apart during insertion of the bundles (3). FIG. 29 illustrates step (ff), wherein the envelope (42) with inserted fiber tows defining prosthetic anchor (36) are fixed to the bone (46) with one or more screws (47) and metal stress-distributing plates (48).

Figure 30:
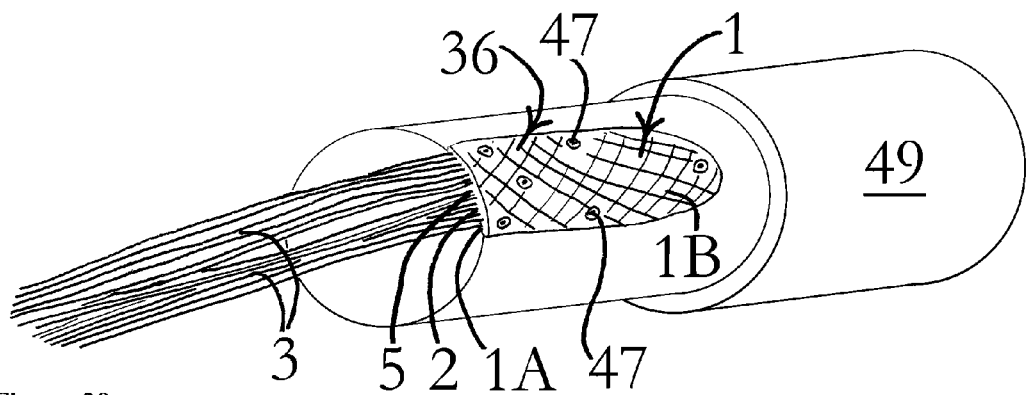
FIG. 30 shows a prosthetic anchor fabricated in accordance with one embodiment of the present invention affixed to a hydraulic energy converter.
Figure 31:
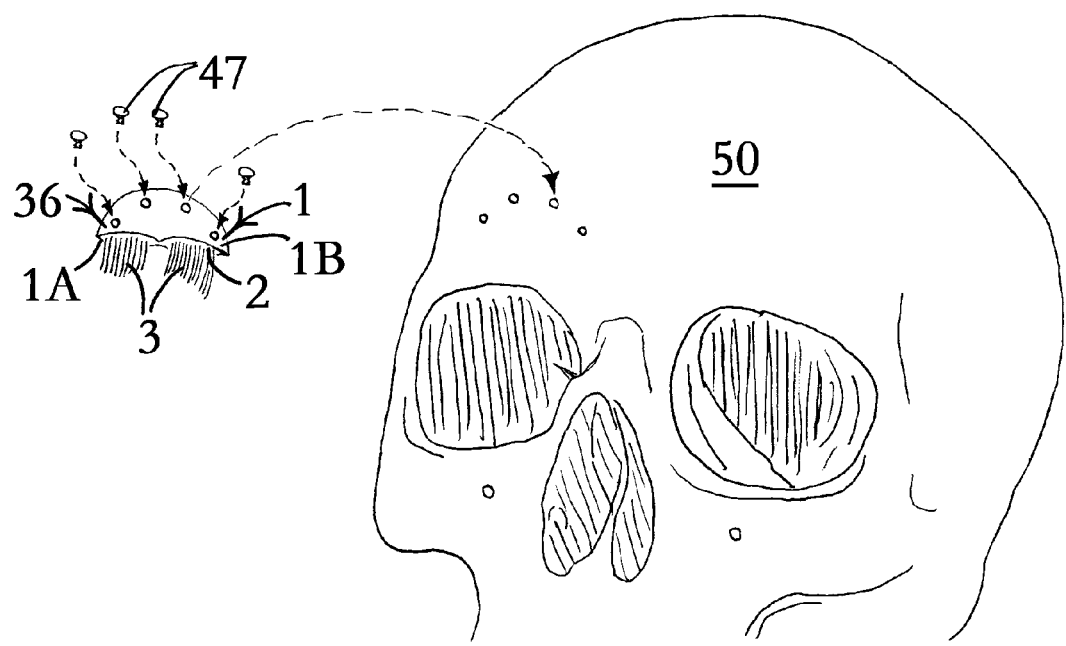
FIG. 31 shows a prosthetic anchor fabricated in accordance with one embodiment of the present invention affixed to a frontal bone.
Figure 32:
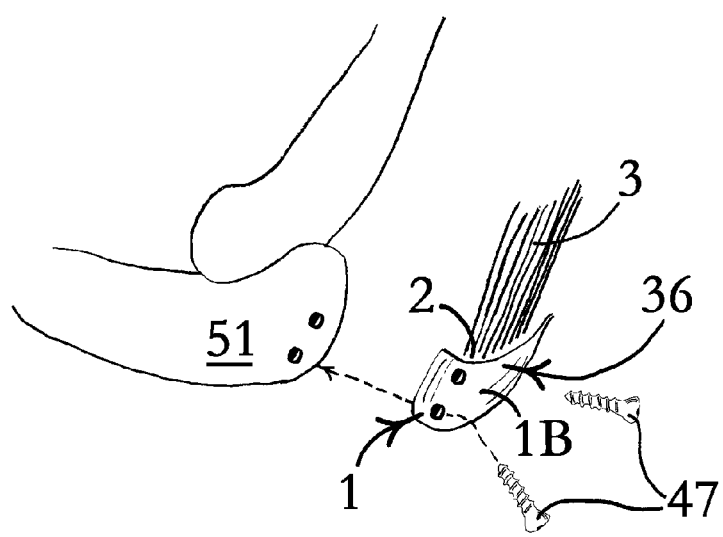
FIG. 32 shows a prosthetic anchor fabricated in accordance with one embodiment of the present invention affixed to an olecranon of an ulna.

FIG. 30 shows a prosthetic anchor (36) according to one embodiment of the present invention as might be applied to a hydraulic or other mechanical energy converter (49). FIG. 31 shows an anchor according to another embodiment of the present invention as might be applied to terminate and fix the prosthetic anchor (36) to a frontal bone (50), such as might be desired in a cosmetic surgical procedure, for example, a brow lift. FIG. 32 shows an anchor according to yet another embodiment of the present invention as might be applied to terminate and fix the prosthetic anchor (36) to an olecranon (51) of an ulna, such as during the reconstruction of a damaged triceps tendon.

In some applications, it may be useful to further adjust a length of the fibers extending from the anchor, for example, by a few millimeters, after implantation. In that regard, and in accordance with various embodiments of the present invention, a wafer-type anchor may be constructed in a manner that is operably moved, in small increments, along the axis of loading and again secured.

Figure 33A:
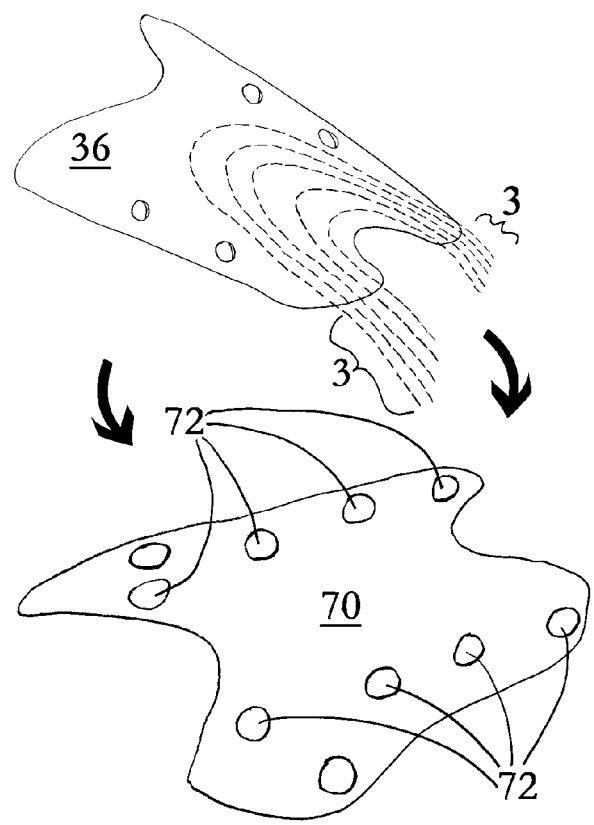
FIG. 33a shows a prosthetic anchor and substrate element in accordance with one embodiment of the present invention.
Figure 33B:
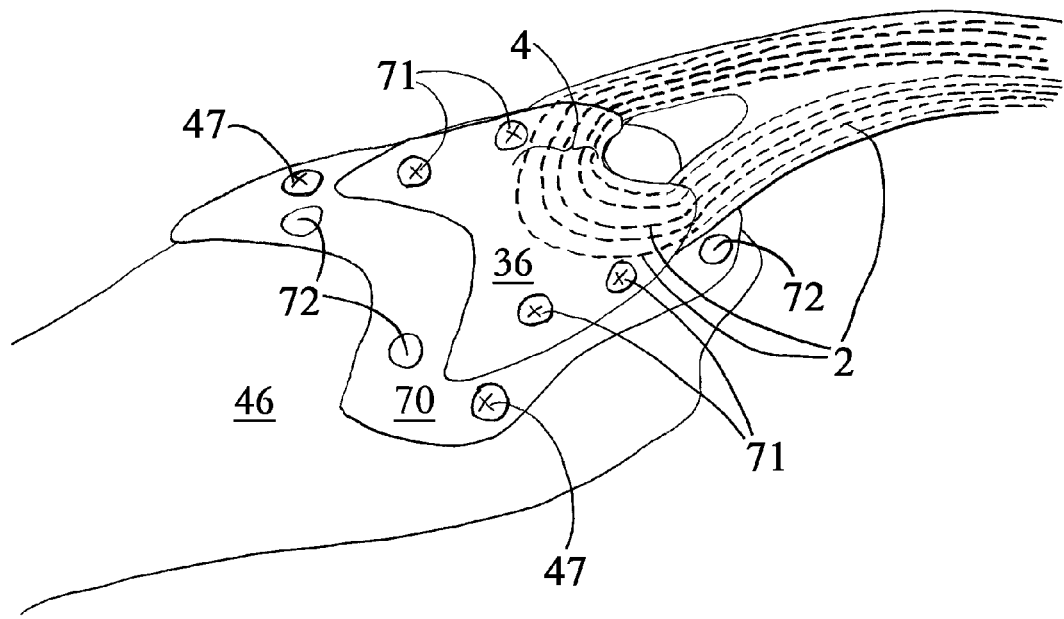
FIG. 33b shows the prosthetic anchor and substrate element of FIG. 33a implanted at a first position on a bone in accordance with the same embodiment of the present invention.

FIG. 33a shows a prosthetic anchor (36) according to another embodiment of the present invention and in which the anchor is configured to be attached to a substrate element (70), for example, with one or more adjustment screws (71) in the prosthetic anchor (36) and an array or series of threaded holes (72) in the substrate element (70) (see FIG. 33b). Prosthetic devices comprising the substrate element (70) may be, but are not limited to, orthopaedic bone plates, artificial bones, and mechanical devices.

FIG. 33b shows the prosthetic anchor (36) attached to the substrate element (70) by way of the adjustment screws (71).

For illustration, the substrate element (70) shown is a bone plate that is attached to a bone (46) with the screws (47). The position of the prosthetic anchor (36) with respect to the substrate element (70) may be selected from among a plurality of discrete positions by aligning the threaded holes (72), and installing the screws (71) into aligned holes (72) (see FIG. 33a). In this figure, one of multiple positions is shown.

Figure 33C:
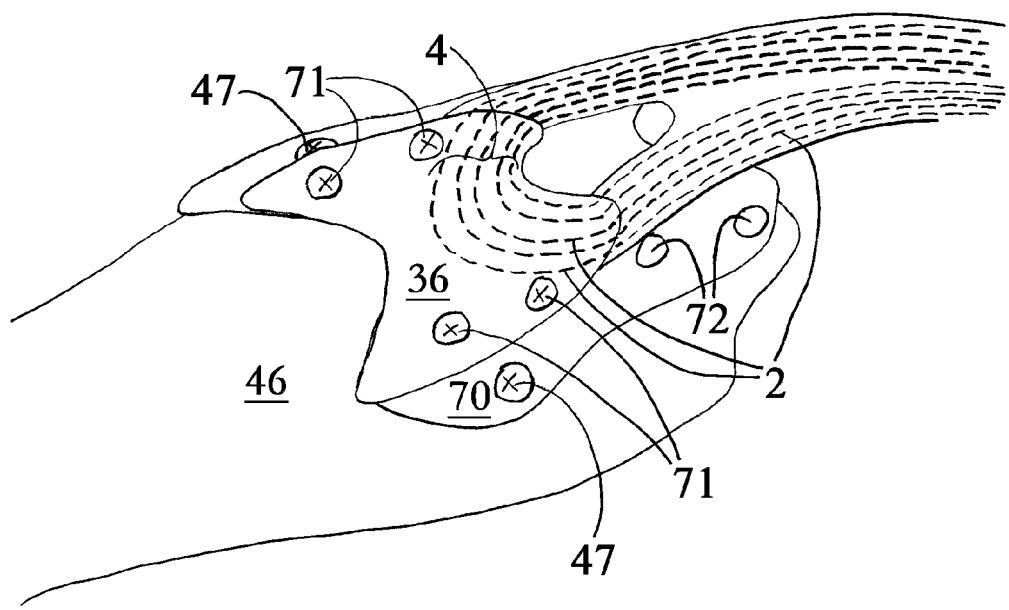
FIG. 33c shows the prosthetic anchor and substrate element of FIG. 33a implanted at a second position on the bone in accordance with the same embodiment of the present invention.

FIG. 33c is similar to FIG. 33b except that a different position is selected, i.e., a different set of holes (72) are aligned and secured.

Figure 34A:
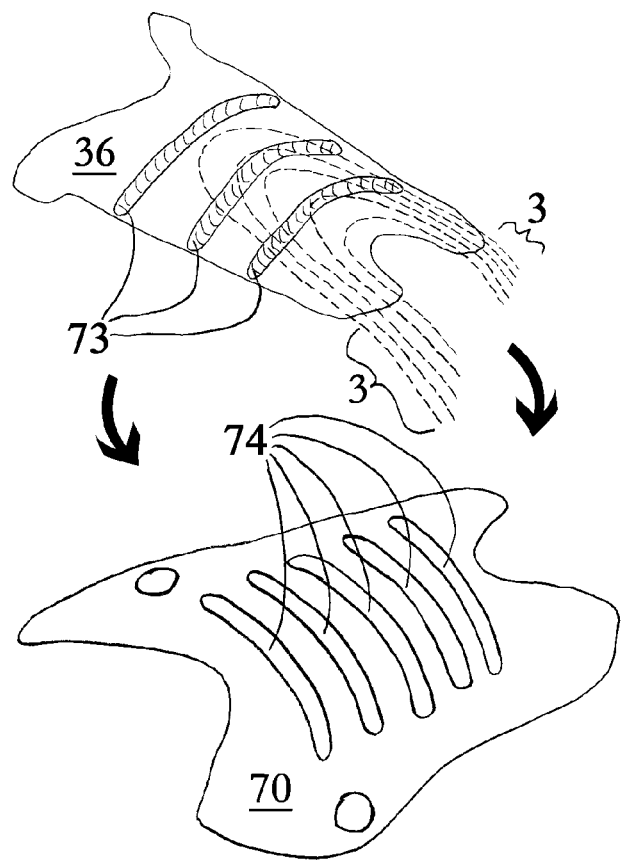
FIG. 34a shows a prosthetic anchor and substrate element with in accordance with another embodiment of the present invention.
Figure 34B:
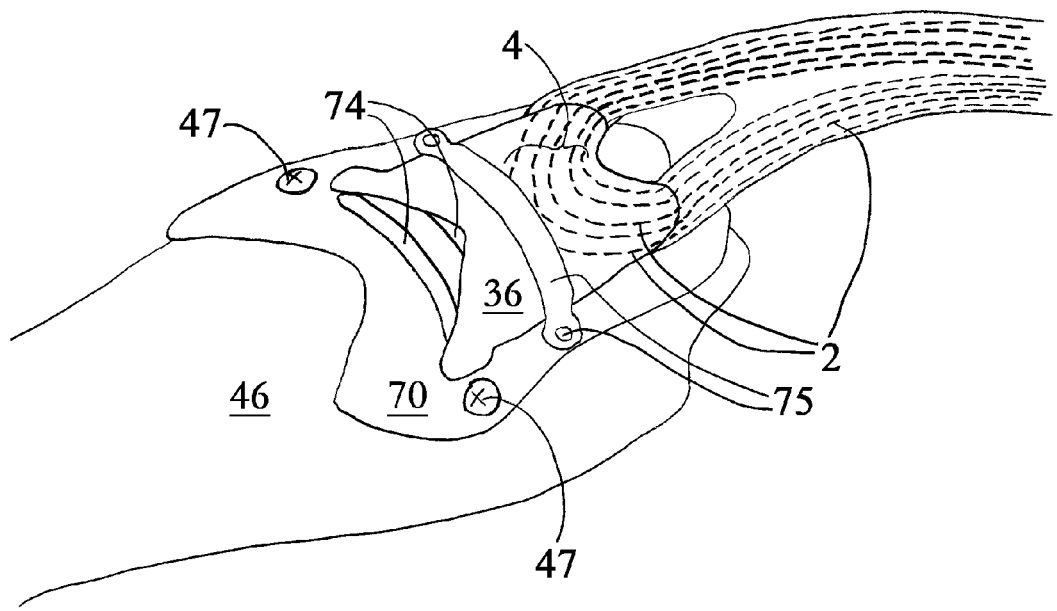
FIG. 34b shows the prosthetic anchor and substrate element of FIG. 34a implanted at a first position on a bone in accordance with the same embodiment of the present invention.

FIG. 34a shows a prosthetic anchor (36) according to another embodiment of the present invention and that is also adjustable. In the present embodiment, the prosthetic anchor (36) includes one or more adjustment ridges (73), which are configured to reside within and mates with a substrate element (70) having an array or series of adjustment grooves (74). As shown in FIG. 34b, the device may further include a fastener (75), such as a screw or a strap equipped with screws, operable to prevent separation of the anchor (36) from the substrate element (70).

FIG. 34b shows the prosthetic anchor (36) mated to the substrate element (70) by aligning the ridges (73) of the anchor (36) with the adjustment grooves (74) of the substrate element. In the particular illustrative example, the substrate element (70) is a bone plate attached to a bone (46) with screws (47). The position of the prosthetic anchor (36) on the substrate element (70) may be selected from among a plurality of discrete positions by aligning the adjustment grooves (74) with a select one or more ridges (73). By placing the prosthetic anchor (36) proximate to the substrate element (70), the fastener (75), when installed, is operable to maintain the ridge(s) (73) in the selected groove(s) (74). The ridges (73) and grooves (74), with or without the fastener (75), resist sliding of the prosthetic anchor (36) with respect to the substrate element (70).

Figure 34C:
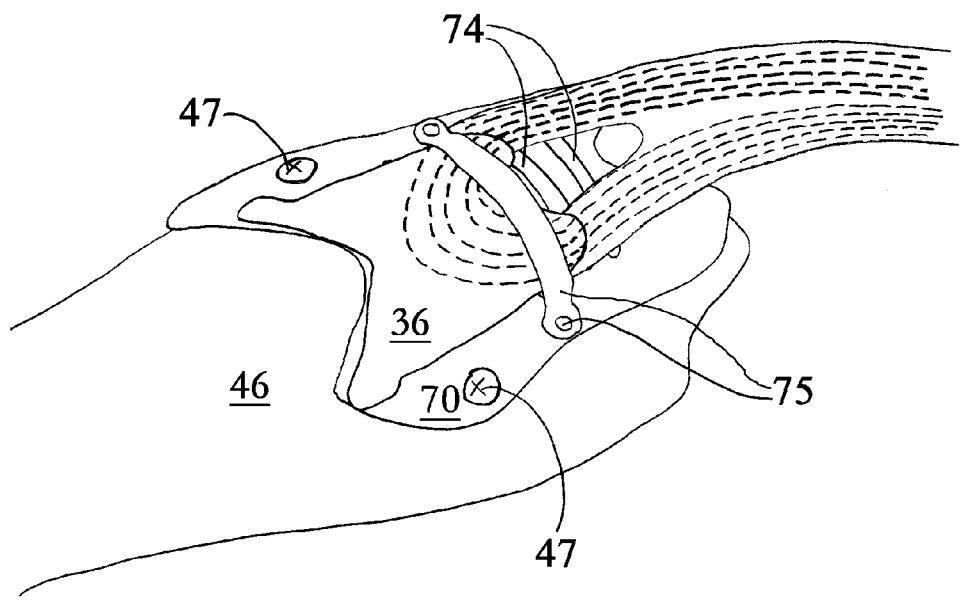
FIG. 34c shows the prosthetic anchor and substrate element of FIG. 34a implanted at a second position on the bone in accordance with the same embodiment of the present invention.

FIG. 34c is similar to the arrangement in FIG. 34b, except that the ridges (73) and the grooves (74) are aligned to a different, selected one position.

In yet another embodiment that is not necessarily shown herein, the prosthetic anchor (36) may include one or more adjustment grooves (74) instead of the one or more adjustment ridges (73) while the substrate element (70) includes adjustment ridges (73) instead of adjustment grooves (74).

Figure 35A:
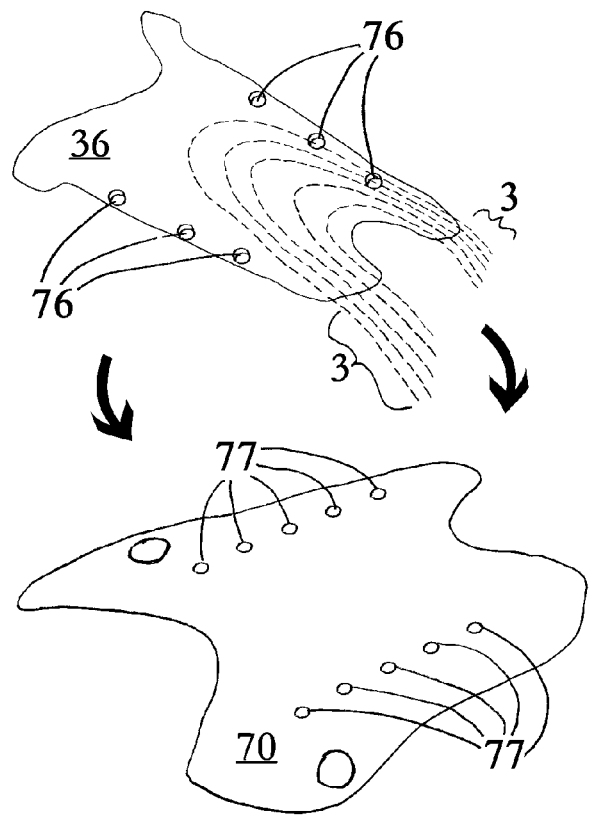
FIG. 35a shows a prosthetic anchor and substrate element with in accordance with yet another embodiment of the present invention.
Figure 35B:
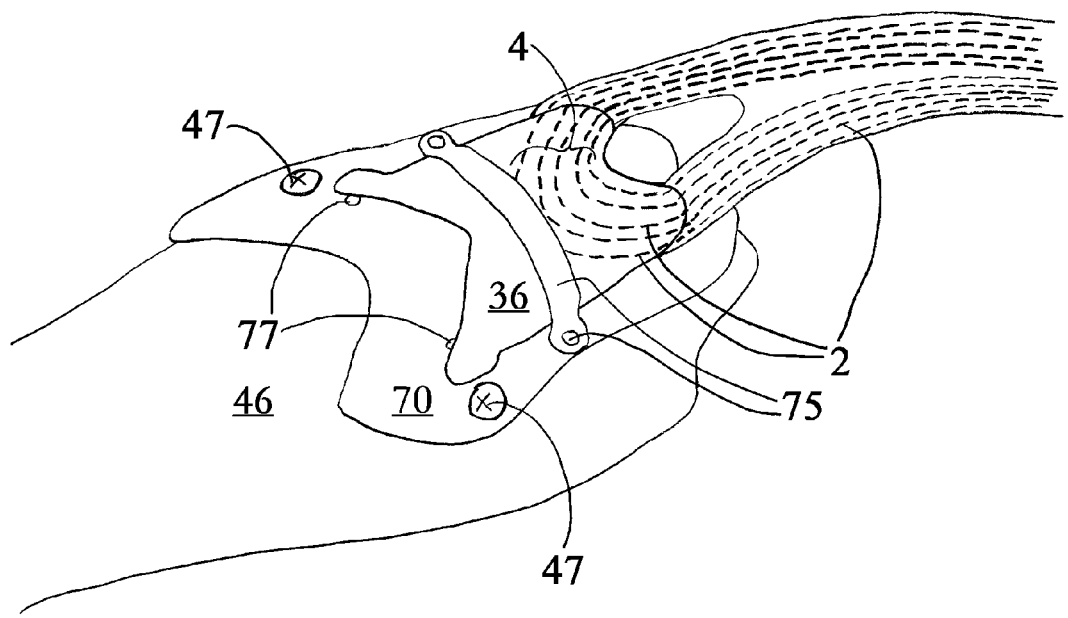
FIG. 35b shows the prosthetic anchor and substrate element of FIG. 35a implanted at a first position on a bone in accordance with the same embodiment of the present invention.

FIG. 35a shows a prosthetic anchor (36) according to another embodiment of the present invention, in which the prosthetic anchor (36) includes one or more adjustment pegs (76) operable to mate with an array or series of adjustment sockets (77) of the substrate element (70). The adjustment pegs (76) and adjustment sockets (77), respectively, perform the same functions as the adjustment ridges (73) and the adjustment grooves (74) as described above. As shown in FIG. 35b, the anchor (36) may further include a fastener (75) that is similar to the fastener previously described.

FIG. 35b shows the prosthetic anchor (36) aligned with and secured to the substrate element (70).

Figure 35C:
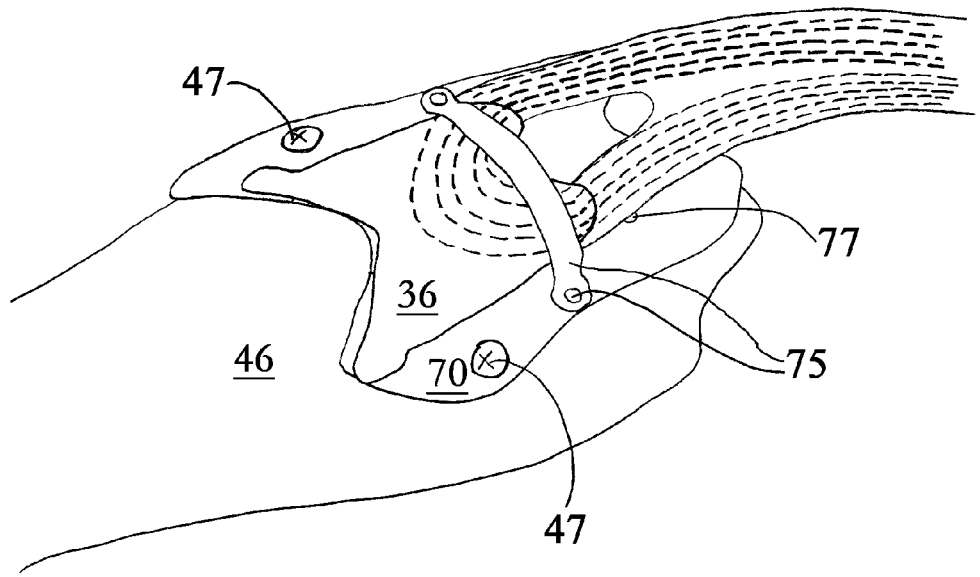
FIG. 35c shows the prosthetic anchor and substrate element of FIG. 35a implanted at a second position on the bone in accordance with the same embodiment of the present invention.

FIG. 35c is similar to FIG. 35b but for the prosthetic anchor (36) is aligned with and secured to the substrate element (70) at a different selected one position.

Figure 36:
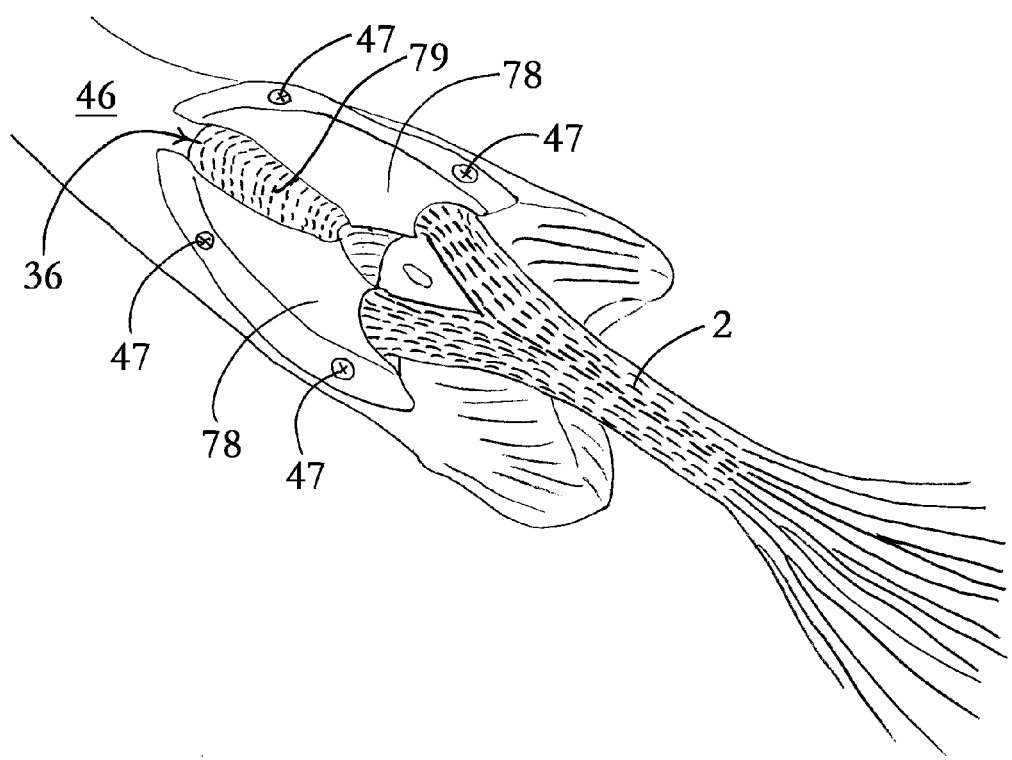
FIG. 36 shows a prosthetic anchor having a partial envelope in accordance with one embodiment of the present invention.

Further, there may be some clinical applications in which further reduction in a thickness of a medial portion of the wafer anchor, such as at an apex of the horseshoe-shaped pattern of embedded fibers, would be advantageous. FIG. 36 shows a prosthetic anchor (36) according to still another embodiment of the present invention and including partial envelopes (78) for reducing the thickness of the middle region. As is shown, two or more partial envelopes (78) may, together, replace the semi-rigid envelope (42) that was described in detail above. In that regard, the two or more partial envelopes (78) may be similar in function and form as the semi-rigid envelope (42) but for having a discontinuity or gap configured to maintain an uncovered middle region (79) of the medial portion of the prosthetic anchor (36). In the area of the discontinuity or gap, only the elastomer-impregnated fiber bundles span between two hemi-envelopes (78). Including the discontinuity or gap reduces the thickness of the envelope-covered anchor (36) in the middle region (79) as compared to the semi-rigid, fiber-composite envelope (42), and thus may be advantageous in some clinical applications, such as replacing of a tendon at the ridge of a bone. The illustrative envelope configuration may also provide more flexibility within the middle region (79), which would provide greater adaptability to anatomical differences. Like the semi-rigid envelope (42), the partial envelopes (78) may be constructed from metal, a fiber composite, or other materials that are suitable for contributing structural stability to the prosthetic anchor (36).

In another embodiment not particularly shown herein, the partial envelopes (78) may also replace the deep membrane (7), the superficial membrane (8), or both and in a manner that is similar to replacement of the semi-rigid envelope (42). Furthermore, it would be readily understood that any combination of the deep membrane (7), the superficial membrane (8), and the fiber composite envelope (42) may alternatively, or additionally, be replaced.

Often, it is necessary or desirable to transmit force or power from a muscle to a location that is distant to, or spaced away from the muscle. It would also be advantageous to preserve the continuity of the prosthetic fibers between the muscle and the distant location.

Figure 37:
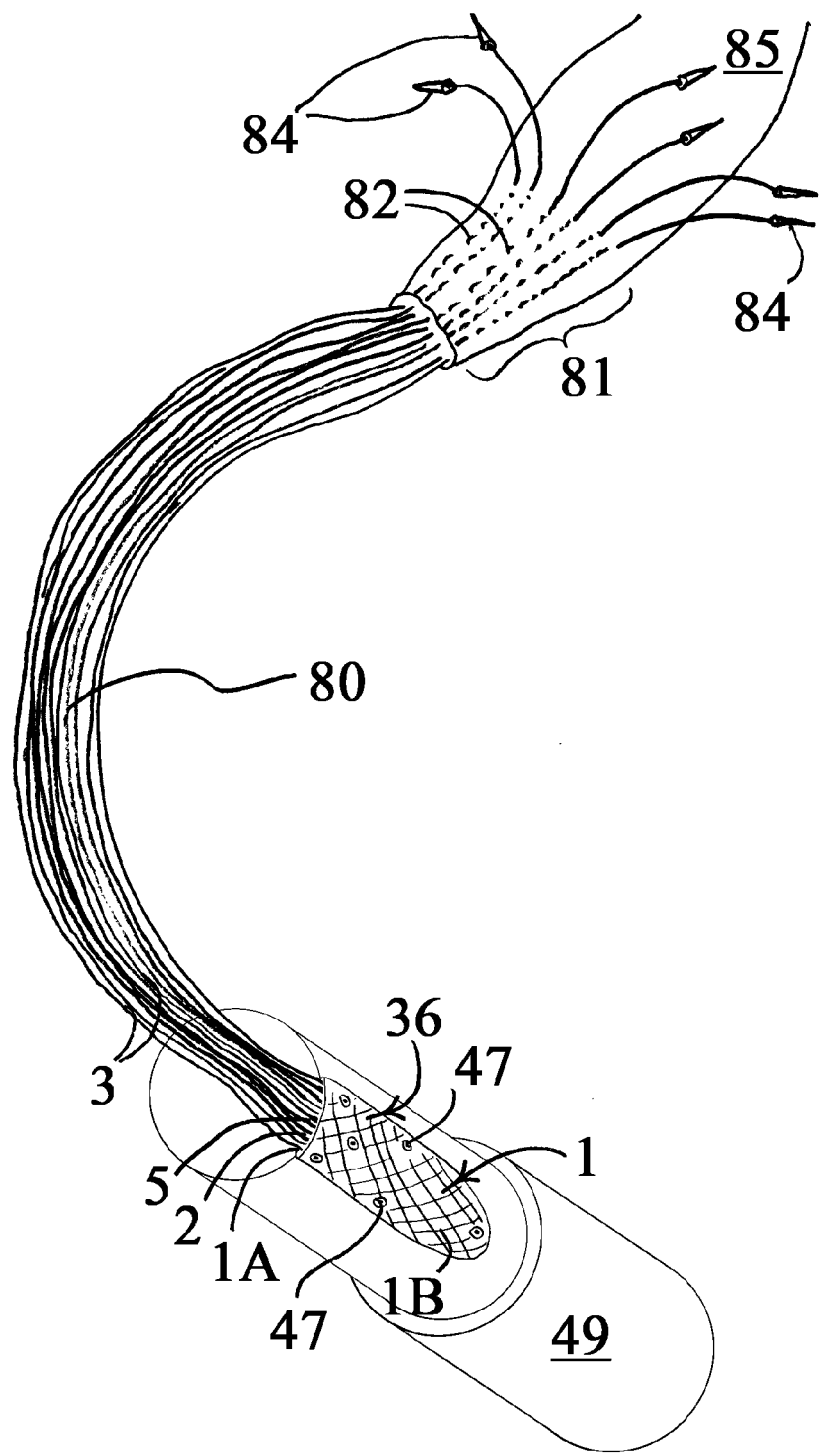
FIG. 37 shows a prosthetic anchor having an elongated tension element, a muscle insertion element, and fiber continuity in accordance with one embodiment of the present invention.

FIG. 37 shows a prosthetic anchor (36) in accordance with another embodiment of the present invention and including an elongated tension element (80). The elongated tension element (80) is configured to transmit a force or work from a muscle (85) to a distant location. A muscle insertion element (81) provides a suitable load-bearing connection to the muscle (85) and may also be integrated with the anchor (36). As shown the wafer-like structure of the anchor is converted to a cylindrical, ribbon, or other shape. The elongated tensile elements (80) may extend from the anchor with the same cylindrical, ribbon, or other shape as the anchor. The muscle insertion element (81) may include a plurality of bundles (82), each having a large number of filaments not shown. Each bundle (82) may also include a needle (84), or other penetrating device, for directing the bundle (82) into and/or through the muscle (85). The filaments may be twisted, but are dispersible, i.e., not braided nor otherwise constrained, so as to promote and facilitate the in-growth of tissue into and amongst the filaments of the bundles (82). Further, no type of restraint that might limit the entry of ingrowing tissue within the bundles (82) and amongst the filaments, nor any braiding, is present in, among, or around the bundles (82) or fine filaments in the muscle insertion element (81). Each filament may be continuous, not only throughout a particular bundle (82) but also through the elongated tensile element (80) and central layer (1) as an embedded fiber (2).

In this way, the plurality of fibers may be operable to couple a contracting muscle to a stable load-bearing tensile power conduit for transmitting a force or power to a location of the body that is spaced away from the muscle. The power conduit may, in turn, be coupled to a power consuming device or other as necessary or desired. For example, such power transmission may be useful in the direct or indirect powering of artificial hearts, ventricular assist devices, or paralytic rehabilitation technology. As compared to conventional electrical or hydraulic energy transmitting systems, the elongated tensile element (80) may avoid the need for a mechanical energy converter. Alternatively, if the elongated tensile element (80) is used in conjunction with a mechanical energy converter, then the elongated tensile element (80) may allow the converter to be placed at a location within the body that would better support the bulk of the converter or that would present fewer problems that locating the converter at the surgical location.

While the present invention has been illustrated by the description of the various embodiments thereof, and while the embodiments have been described in considerable detail, it is not intended to restrict or in any way limit the scope of the appended claims to such detail. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of Applicant's general inventive concept.

What is claimed is:

1. A prosthetic anchor system configured to be attached to a natural or prosthetic structure of a human or animal, comprising:
an anchor comprising a central layer having top and bottom surfaces and; a plurality of fiber bundles, each of the plurality of fiber bundles having a medial portion embedded within the central layer to substantially define a generally horseshoe-shaped pattern that is situated concentrically with respect to another of the plurality of bundles;
a substrate element configured to be secured to the natural or prosthetic structure and to receive the bottom surface of the central layer, the substrate element having a plurality of positional elements defining a plurality of discrete positions selectable for the anchor relative to the substrate element; and
a securing element configured to couple the anchor to the substrate element selectively in one of the plurality of discrete positions; wherein the central layer is a wafer-like structure, the wafer-like structure defines a plurality of pathways, and the plurality of fiber bundles are embedded respectively within the plurality of pathways.

2. The prosthetic anchor system of claim 1, wherein the securing element comprises:
at least one rib on the top surface of the central layer; and
a plurality of grooves on the substrate element, each of the plurality of grooves configured to receive the at least one rib,
wherein the at least one rib is aligned with a select one of the plurality of grooves to define the plurality of positions.

3. The prosthetic anchor system of claim 2, wherein the anchor is secured to the substrate element after the at least one rib is aligned with the select one of the plurality of grooves.

4. The prosthetic anchor system of claim 3, wherein the anchor is further secured to the substrate element with at least one screw or bolt.

5. The prosthetic anchor system of claim 3, wherein the anchor is secured to the substrate element with a fastener, the fastener extending across the anchor and being coupled to the substrate element to further secure the anchor.

6. The prosthetic anchor system of claim 1, wherein the securing element comprises:
a first plurality of holes in the central layer;
a second plurality of holes in the substrate element, wherein at least one of the first plurality of holes is aligned with a select one of the second plurality of holes in the substrate element.

7. The prosthetic anchor system of claim 6, wherein the aligned one of the first plurality of holes and the select one of the second plurality of holes are secured with a screw or a bolt.

8. The prosthetic anchor system of claim 1, wherein the top and bottom surfaces sandwich the medial portions of the plurality of fiber bundles therebetween.

* * * * *